US009751859B2

(12) United States Patent
Chen et al.

(10) Patent No.: US 9,751,859 B2
(45) Date of Patent: Sep. 5, 2017

(54) PROCESS FOR PREPARING AN ANTI-CANCER AGENT, 1-((4-(4-FLUORO-2-METHYL-1H-INDOL-5-YLOXY)-6-METHOXYQUINOLIN-7-YLOXY)METHYL)CYCLOPROPANAMINE, ITS CRYSTALLINE FORM AND ITS SALTS

(71) Applicant: Advenchen Pharmaceuticals, LLC, Moorpark, CA (US)

(72) Inventors: Guoqing Paul Chen, Westlake Village, CA (US); Changren Yan, Camarillo, CA (US)

(73) Assignee: Advenchen Pharmaceuticals, LLC, Moorpark, CA (US)

( * ) Notice: Subject to any disclaimer, the term of this patent is extended or adjusted under 35 U.S.C. 154(b) by 0 days.

(21) Appl. No.: 15/143,630

(22) Filed: May 2, 2016

(65) Prior Publication Data
US 2016/0326138 A1    Nov. 10, 2016

Related U.S. Application Data

(60) Provisional application No. 62/156,734, filed on May 4, 2015, provisional application No. 62/205,272, filed on Aug. 14, 2015.

(51) Int. Cl.
*C07D 401/12* (2006.01)
*C07C 57/145* (2006.01)
(Continued)

(52) U.S. Cl.
CPC .......... *C07D 401/12* (2013.01); *A61K 31/337* (2013.01); *A61K 31/4709* (2013.01); *A61K 31/555* (2013.01); *A61K 33/24* (2013.01); *A61K 39/3955* (2013.01); *A61K 45/06* (2013.01); *C07C 55/10* (2013.01); *C07C 57/145* (2013.01); *C07K 16/22* (2013.01); *A61K 2039/505* (2013.01); *C07K 2317/76* (2013.01)

(58) Field of Classification Search
CPC ...... C07D 401/12; C07C 55/10; C07C 57/145
(Continued)

(56) References Cited

FOREIGN PATENT DOCUMENTS

| CN | 102344438 | 2/2012 |
|---|---|---|
| WO | WO 2008/112408 | 9/2008 |
| WO | WO 2010/105761 | 9/2010 |
| WO | WO 2014/113616 | 7/2014 |

OTHER PUBLICATIONS

SSCI "what everyone . . . " p. 1-6 (2000).*
Bello, E. et al., E-3810 Is a Potent Dual Inhibitor of VEGFR and FGFR thatExerts Antitumor Activity in Multiple Preclinical Models, Cancer Research; 71(4), Feb. 15, 2011.
International Preliminary Report on Patentability and Written Opinion received in International patent application No. PCT/US2014/011948, dated Jul. 21, 2015.
(Continued)

*Primary Examiner* — Celia Chang
(74) *Attorney, Agent, or Firm* — Knobbe, Martens, Olson & Bear, LLP

(57) ABSTRACT

The present invention relates a new process to synthesize 1-((4-(4-Fluoro-2-methyl-1H-indol-5-yloxy)-6-methoxy-quinolin-7-yloxy)methyl)cyclopropanamine (AL3818). A stable crystalline form of Al3818 has been prepared. Salts and their crystalline forms of AL3818 have been also prepared. Anti-cancer and optometric activities of AL3818 and its salts have been further tested. New process has been outlined in Scheme I.

(Continued)

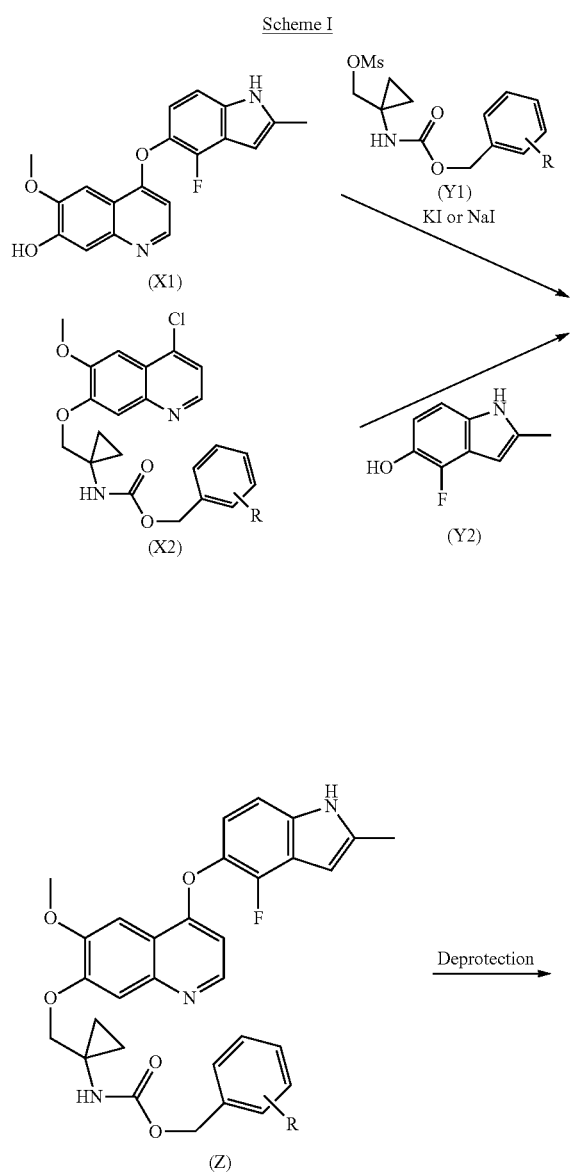

Scheme I

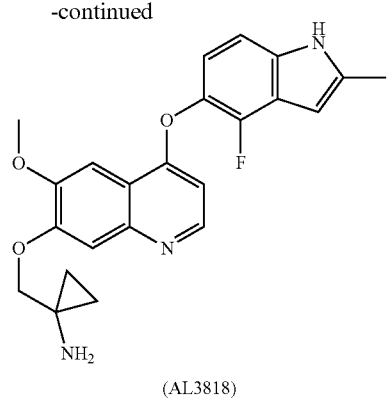

(AL3818)

9 Claims, 13 Drawing Sheets

(51) Int. Cl.
*C07C 55/10* (2006.01)
*A61K 31/4709* (2006.01)
*A61K 45/06* (2006.01)
*A61K 33/24* (2006.01)
*A61K 31/337* (2006.01)
*A61K 39/395* (2006.01)
*C07K 16/22* (2006.01)
*A61K 31/555* (2006.01)
*A61K 39/00* (2006.01)

(58) Field of Classification Search
USPC .................................................. 546/153
See application file for complete search history.

(56) References Cited

OTHER PUBLICATIONS

Sala, F. et al., Development and validation of a high-performance liquid chromatography—tandem mass spectrometry method for the determination of the novel inhibitor of angiogenesis E-3810 in human plasma and its application in a clinical pharmacokinetic study, Journal of Mass Spectrometry, 2011, 46, pp. 1039-1045.
Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.

* cited by examiner

Effect of AL3818 on Tumor volume of human endometrial cancer Ishikawa xenografted athymic nude mice Effect of AL3818 on Relative Tumor volume of human endometrial cancer Ishikawa xenografted athymic nude mice Effect of AL3818 salts combined with Carboplatin (CBX)/Paclitaxel (Taxol) on Tumor volume of human endometrial cancer Ishikawa xenografted athymic nude mice Effect of AL3818 salts combined with Carboplatin (CBX)/Paclitaxel (Taxol) on Relative Tumor volume of human endometrial cancer Ishikawa xenografted athymic nude mice Effects of oral administration of AL3818 on laser-induced CNV Effects of AL3818 (0.15 mg/kg body weight) and intravitreal anti-VEGF antibody on laser-induced CNV

PROCESS FOR PREPARING AN ANTI-CANCER AGENT, 1-((4-(4-FLUORO-2-METHYL-1H-INDOL-5-YLOXY)-6-METHOXYQUINOLIN-7-YLOXY) METHYL)CYCLOPROPANAMINE, ITS CRYSTALLINE FORM AND ITS SALTS

This application claims the benefit of U.S. Provisional Applications 62/156,734 filed on May 4, 2015 and 62/205,272 filed on Aug. 14, 2015

FIELD OF THE INVENTION

The present invention relates a new process to synthesize 1-((4-(4-Fluoro-2-methyl-1H-indol-5-yloxy)-6-methoxyquinolin-7-yloxy)methyl)cyclopropanamine (AL3818). A stable crystalline form of Al3818 has been prepared. Salts and their crystalline forms of AL3818 have been also prepared. Anti-cancer and optometric activities of AL3818 and its salts have been further tested.

BACKGROUND OF THE INVENTION 1-((4-(4-Fluoro-2-methyl-1H-indol-5-yloxy)-6-methoxyquinolin-7-yloxy)-methyl)-cyclopropanamine (AL3818) has been structurally disclosed in WO2008112407 as an agiogenesis inhibitor with few preparation methods.

SUMMARY OF THE INVENTION

Abbreviations and Definitions

The following abbreviations are used and have the meaning below for ease of reference.

EtOH: ethanol, MeOH: methanol, IPA: isopropanol, EtOAc: ethyl acetate, RT: room temperature, DIPEA: diisopropylethylamine, DCM: Dichloromethane, DMF: N,N-dimethylformamide, DMAP: 4-N,N-dimethylaminopyridine, MsCl: methanesulfonyl chloride, THF: tetrahydrofuran, TFA: trifluoroacetic acid, TEA: triethylamine, Pd/C: Palladium on active Carbon, eq: equivalent, g: gram, mg: milligram, ml: milliliter, min: minutes, bis=di: two or double DSC: differential scanning calorimetric, TGA: thermogravimetric analysis, XRPD: X-ray powder diffraction, Exo: exotherm, Endo: endotherm.

ALL: Acute Lymphocytic or Lymphoblastic Leukemias, CLL: Chronic Lymphocytic or Lymphoblastic Leukemias, AML: Acute Myelogenous or Myeloid Leukemias, CML: Chronic Myelogenous or Myeloid Leukemias The term "$C_1$-$C_6$alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "$C_1$-$C_6$alkoxy", as used herein, unless otherwise indicated, includes —$OC_1$-$C_6$alkyl groups wherein $C_1$-$C_6$alkyl is as defined above, such as methoxy and ethoxy.

Invention Scope

The present invention relates a new process to synthesize 1-((4-(4-Fluoro-2-methyl-1H-indol-5-yloxy)-6-methoxyquinolin-7-yloxy)methyl)cyclopropanamine (AL3818) by condensing intermediate (X1) with (Y1) in a solvent at the presence of KI or NaI, or intermediate (X2) with (Y2) in a solvent to form intermediate (Z) which is deprotected to give the final compound (AL3818) in Scheme I. A stable crystalline form of 1-((4-(4-Fluoro-2-methyl-1H-indol-5-yloxy)-6-methoxyquinolin-7-yloxy)-methyl)cyclopropanamine and its salts as well as crystalline forms of salts have also been prepared.

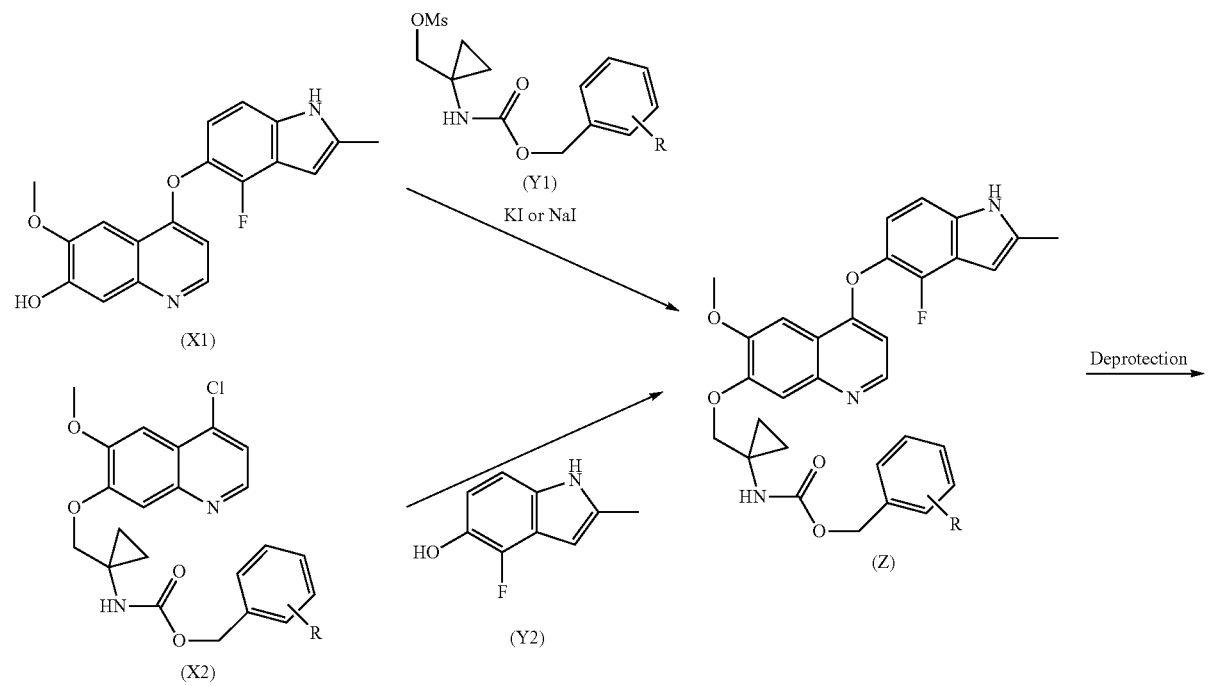

Scheme I

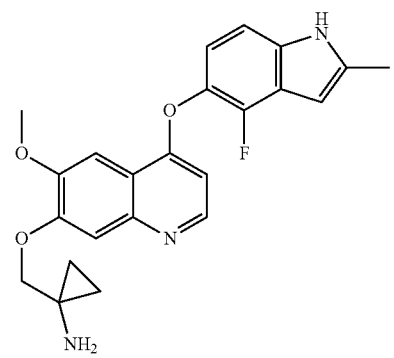

(AL3818)

Wherein, R is selected from H and $C_1$-$C_6$alkoxy.

DETAILED DESCRIPTION OF THE INVENTION

Figure 1:
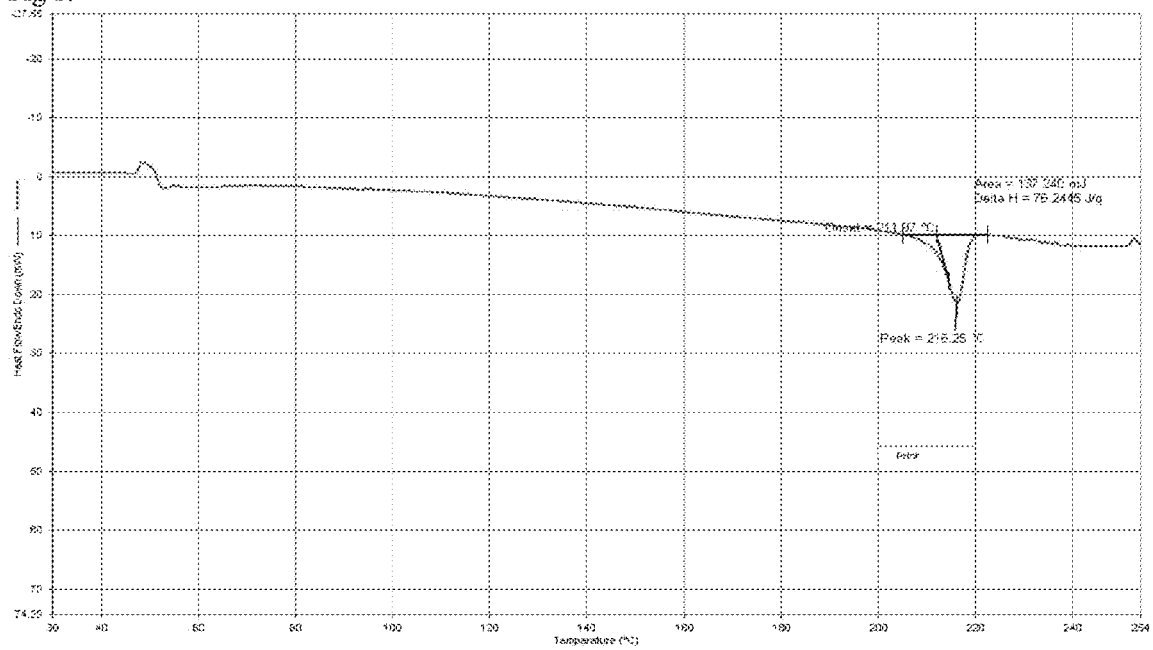
FIG. 1. DSC graph of a crystalline form of 1-((4-(4-Fluoro-2-methyl-1H-indol-5-yloxy)-6-methoxyquinolin-7-yloxy)-methyl)cyclopropanamine FIG. 2. TGA graph of a crystalline form of 1-((4-(4-Fluoro-2-methyl-1H-indol-5-yloxy)-6-methoxyquinolin-7-yloxy)-methyl)cyclopropanamine FIG. 3. XRPD graph of a crystalline form of 1-((4-(4-Fluoro-2-methyl-1H-indol-5-yloxy)-6-methoxyquinolin-7-yloxy)-methyl)cyclopropanamine FIG. 4. DSC graph of a crystalline form of bishydrochloride acid salt of 1-((4-(4-Fluoro-2-methyl-1H-indol-5-yloxy)-6-methoxyquinolin-7-yloxy)-methyl)cyclopropanamine FIG. 5. TGA graph of a crystalline form of bishydrochloride acid salt of 1-((4-(4-Fluoro-2-methyl-1H-indol-5-yloxy)-6-methoxyquinolin-7-yloxy)-methyl)cyclopropanamine FIG. 6. XRPD graph of a crystalline form of bishydrochloride acid salt of 1-((4-(4-Fluoro-2-methyl-1H-indol-5-yloxy)-6-methoxyquinolin-7-yloxy)-methyl)cyclopropanamine FIG. 7. DSC graph of a crystalline form of bishydrochloridehydrate acid salt of 1-((4-(4-Fluoro-2-methyl-1H-indol-5-yloxy)-6-methoxyquinolin-7-yloxy)-methyl)cyclopropanamine FIG. 8. TGA graph of a crystalline form of bishydrochloridehydrate acid salt of 1-((4-(4-Fluoro-2-methyl-1H-indol-5-yloxy)-6-methoxyquinolin-7-yloxy)-methyl)cyclopropanamine FIG. 9. XRPD graph of a crystalline form of bishydrochloridehydrate acid salt of 1-((4-(4-Fluoro-2-methyl-1H-indol-5-yloxy)-6-methoxyquinolin-7-yloxy)-methyl)cyclopropanamine FIG. 10. DSC graph of a crystalline form of bismaleic acid salt of 1-((4-(4-Fluoro-2-methyl-1H-indol-5-yloxy)-6-methoxyquinolin-7-yloxy)-methyl)cyclopropanamine FIG. 11. TGA graph of a crystalline form of bismaleic acid salt of 1-((4-(4-Fluoro-2-methyl-1H-indol-5-yloxy)-6-methoxyquinolin-7-yloxy)-methyl)cyclopropanamine FIG. 12. XRPD graph of a crystalline form of bismaleic acid salt of 1-((4-(4-Fluoro-2-methyl-1H-indol-5-yloxy)-6-methoxyquinolin-7-yloxy)-methyl)cyclopropanamine FIG. 13. DSC graph of a crystalline form of succinic acid salt of 1-((4-(4-Fluoro-2-methyl-1H-indol-5-yloxy)-6-methoxyquinolin-7-yloxy)-methyl)cyclopropanamine FIG. 14. TGA graph of a crystalline form of succinic acid salt of 1-((4-(4-Fluoro-2-methyl-1H-indol-5-yloxy)-6-methoxyquinolin-7-yloxy)-methyl)cyclopropanamine FIG. 15. XRPD graph of a crystalline form of succinic acid salt of 1-((4-(4-Fluoro-2-methyl-1H-indol-5-yloxy)-6-methoxyquinolin-7-yloxy)-methyl)cyclopropanamine FIG. 16. Effect of AL3818 and its salts on human endometrial cancer Ishikawa xenografted athymic mice FIG. 17. Effect of AL3818 salts combined with Carboplatin (CBX)/Paclitaxel (Taxol) on human endometrial cancer Ishikawa xenografted athymic mice FIG. 18. Effects of oral administration of AL3818 on laser-induced CNV FIG. 19. Effects of AL3818 (0.15 mg/kg body weight) and intravitreal anti-VEGF antibody on laser-induced CNV

The present invention relates a new process to synthesize 1-((4-(4-Fluoro-2-methyl-1H-indol-5-yloxy)-6-methoxyquinolin-7-yloxy)methyl)cyclopropanamine (AL3818) by condensing intermediate (X1) with (Y1) in a solvent at the presence of KI or NaI, or intermediate (X2) with (Y2) in a solvent to form intermediate (Z) which is deprotected to give the final compound (AL3818) in Scheme I.

Wherein, R is selected from H and $C_1$-$C_6$alkoxy, preferably selected from H and —OMe;

The present invention relates to prepare a stable crystalline form of 1-((4-(4-Fluoro-2-methyl-1H-indol-5-yloxy)-6-methoxyquinolin-7-yloxy)methyl)cyclopropanamine;

The present invention relates to prepare the salts or stable crystalline salt forms of 1-((4-(4-Fluoro-2-methyl-1H-indol-5-yloxy)-6-methoxyquinolin-7-yloxy)methyl);

The present invention relates to bishydrochloride acid, bishydrochloridehydrate acid, bismaleic acid and succinic acid salt, and their stable crystalline salt forms or stable crystalline free base form of 1-((4-(4-Fluoro-2-methyl-1H-indol-5-yloxy)-6-methoxyquinolin-7-yloxy)methyl)-cyclopropanamine.

The present invention relates to prepare a pharmaceutical composition that comprises a stable crystalline form of 1-((4-(4-Fluoro-2-methyl-1H-indol-5-yloxy)-6-methoxyquinolin-7-yloxy)methyl)cyclopropanamine and a pharmaceutically acceptable carrier;

The present invention relates to prepare a pharmaceutical composition that comprises the salts or stable crystalline salt forms of 1-((4-(4-Fluoro-2-methyl-1H-indol-5-yloxy)-6-methoxy-quinolin-7-yloxy)-methyl)cyclopropanamine and a pharmaceutically acceptable carrier;

The present invention relates to a stable crystalline form or the salts or stable crystalline salt forms of 1-((4-(4-Fluoro-2-methyl-1H-indol-5-yloxy)-6-methoxyquinolin-7-yloxy)methyl)-cyclopropanamine for a method in treating a neoplastic disease;

The present invention relates to a stable crystalline form or the salts or stable crystalline salt forms of 1-((4-(4-Fluoro-2-methyl-1H-indol-5-yloxy)-6-methoxyquinolin-7-yloxy)methyl)-cyclopropanamine for use in the manufacture of a medicament for a method in the treating a neoplastic disease;

The present invention relates to a stable crystalline form or the salts or stable crystalline salt forms of 1-((4-(4-Fluoro-2-methyl-1H-indol-5-yloxy)-6-methoxyquinolin-7-yloxy)methyl)-cyclopropanamine for a method in mono therapy or combing with chemotherapy agents, selected from platinum based or taxane based agents in treating solid tumors, selected from lung, renal, colorectal, gastric, melanoma, head/neck, thyroid, pancreatic, liver, prostate, bladder, brain, sarcoma, breast, ovarian, cervical and endometrial cancers; and blood cancers, selected from ALL, CLL, AML, CML and Multiple Myeloma;

The present invention relates to bishydrochloride acid, bishydrochloridehydrate acid, bismaleic acid and succinic acid salt, and their stable crystalline salt forms or stable crystalline free base form of 1-((4-(4-Fluoro-2-methyl-1H-indol-5-yloxy)-6-methoxyquinolin-7-yloxy)methyl)-cyclopropanamine for a methos in mono therapy or combing with chemotherapy agents, selected from platinum based or taxane based agents in treating solid tumors, selected from lung, renal, colorectal, gastric, melanoma, head/neck, thyroid, pancreatic, liver, prostate, bladder, brain, sarcoma, breast, ovarian, cervical and endometrial cancers; and blood cancers, selected from ALL, CLL, AML, CML and Multiple Myeloma;

The present invention relates to bishydrochloride acid, bishydrochloridehydrate acid, bismaleic acid and succinic acid salt, and their stable crystalline salt forms or stable crystalline free base form of 1-((4-(4-Fluoro-2-methyl-1H-indol-5-yloxy)-6-methoxyquinolin-7-yloxy)methyl)-cyclopropanamine for a method in mono therapy or combing with chemotherapy agents, selected from platinum based or taxane based agents in treating lung, colorectal, gastric, thyroid, pancreatic, liver, prostate, sarcoma, breast, ovarian, cervical and endometrial cancers.

The present invention relates a new process to synthesize 1-((4-(4-Fluoro-2-methyl-1H-indol-5-yloxy)-6-methoxyquinolin-7-yloxy)methyl)cyclopropanamine (AL3818) by condensing intermediate (X1) with (Y1) in a solvent at the presence of KI or NaI to form intermediate (Z) which is deprotected to give the final compound (AL3818) according to Process A.

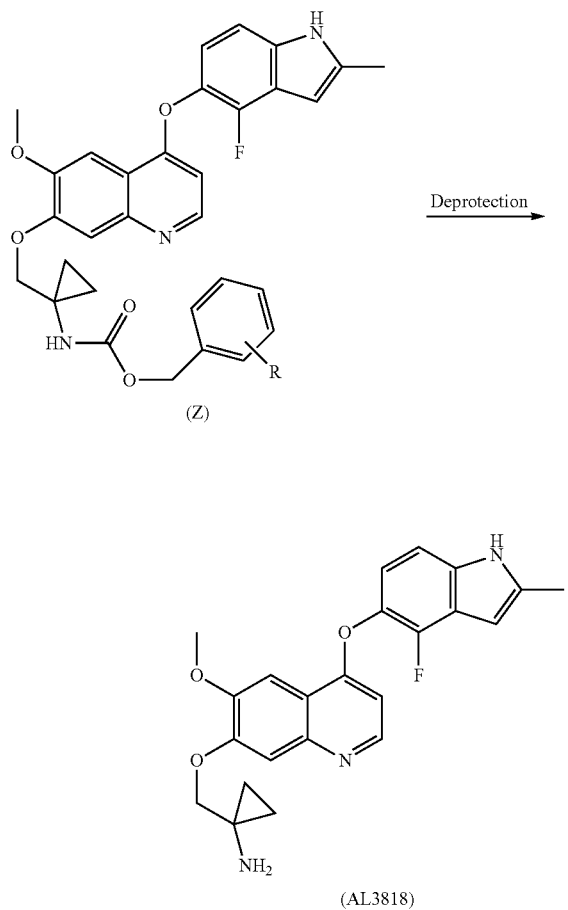

R is selected from H and C1-C6 alkoxy

The final compound (AL3818) was prepared according to Process A1 when R is H by deprotecting intermediate (Z-1) with HCOONH$_4$ (ammonium formate) and Pd/C in an alcoholic solvent, such as MeOH, at 25° C.-80° C. for 0.1-4 hours. (Z-1) was prepared by reacting intermediate (X1) with (Y1-1) at the presence of KI or NaI with K$_2$CO$_3$ in a solvent, such as acetone or DMF, at a temperature of 60° C.-160° C. for 2-24 hours.

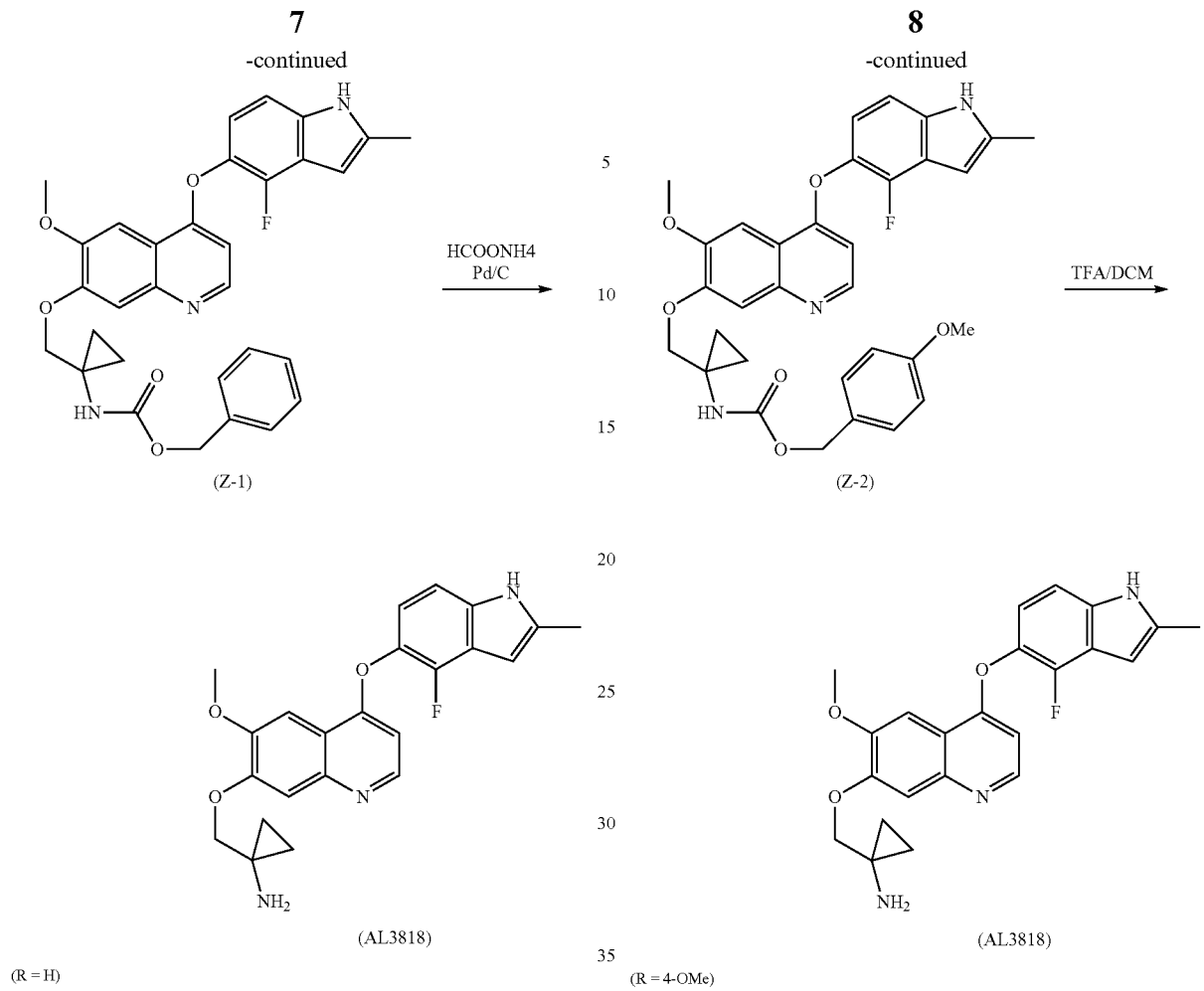

The final compound (AL3818) was prepared according to Process A2 when R is 4-OMe by deprotecting intermediate (Z-2) with TFA in DCM at 0° C.-30° C. for 1-24 hours. (Z-2) was prepared by reacting intermediate (X1) with (Y1-2) at the presence of KI or NaI with K₂CO₃ in a solvent, such as acetone or DMF, at a temperature of 60° C.-160° C. for 2-24 hours.

The present invention relates a new process to synthesize 1-((4-(4-Fluoro-2-methyl-1H-indol-5-yloxy)-6-methoxy-quinolin-7-yloxy)methyl)cyclopropanamine (AL3818) by reacting intermediate (X2) with (Y2) in a solvent to form intermediate (Z) which is deprotected to give the final compound (AL3818) according to Process B.

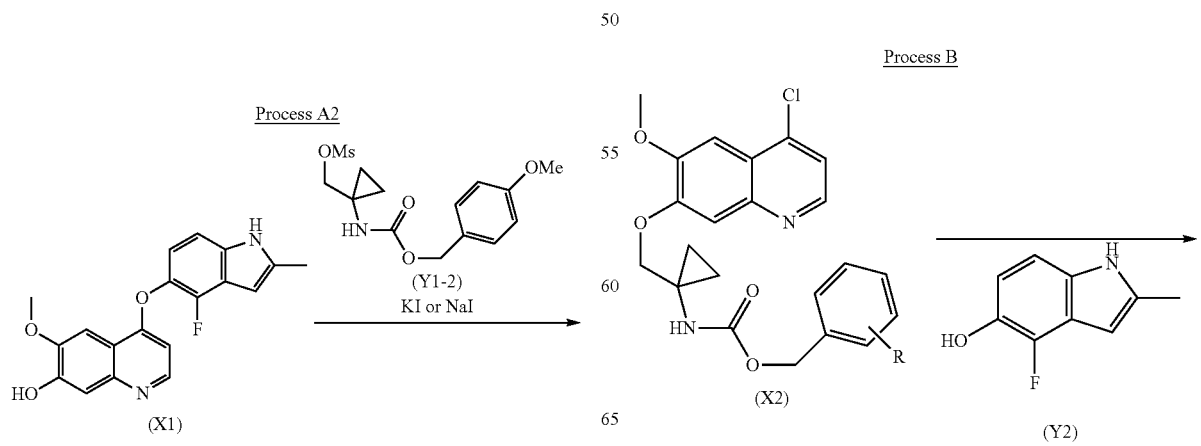

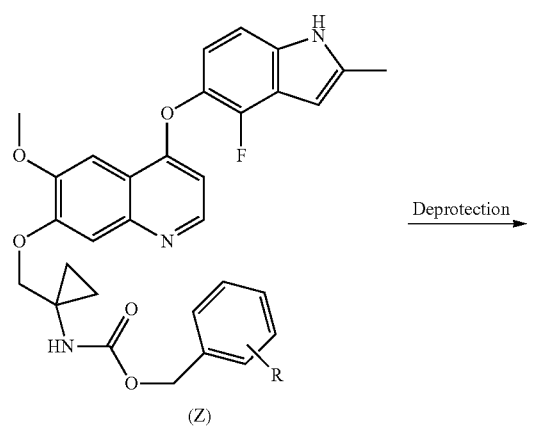

(Z)

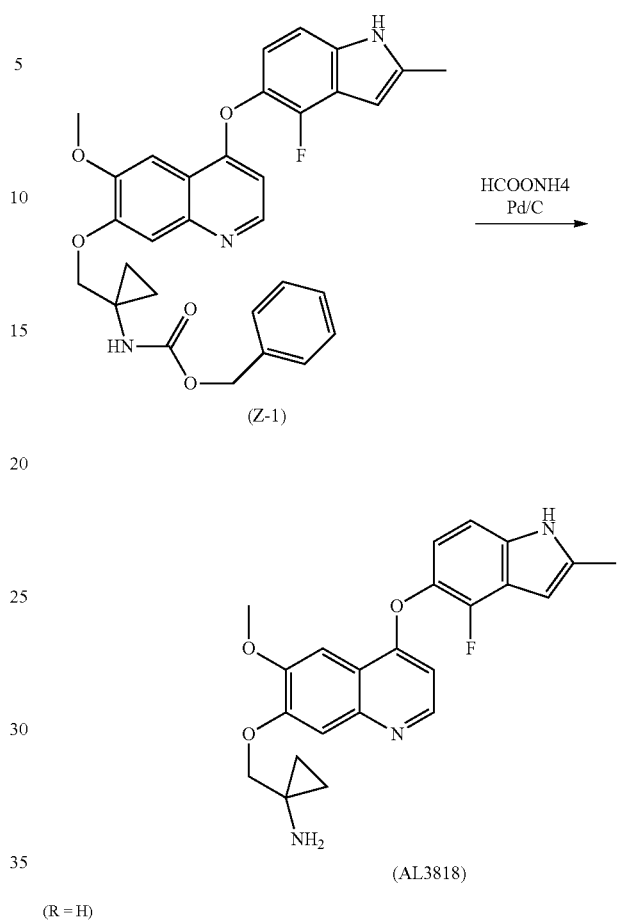

(Z-1)

(AL3818)

(R = H)

(AL3818)

The final compound (AL3818) was prepared according to Process B1 when R is H by deprotecting intermediate (Z-1) with HCOONH$_4$ (ammonium formate) and Pd/C in an alcoholic solvent, such as MeOH, at 25° C.-80° C. for 0.1-4 hours. (Z-1) was prepared by reacting intermediate (X2-1) with (Y2) in a solvent, such as pyridine or lutidine, at a temperature of 60° C.-160° C. for 1-12 hours.

The final compound (AL3818) was prepared according to Process B2 when R is 4-OMe by deprotecting intermediate (Z-2) with TFA in DCM at 0° C.-30° C. for 1-24 hours. (Z-2) was prepared by reacting intermediate (X2-2) with (Y2) in a solvent, such as pyridine or lutidine, at a temperature of 60° C.-160° C. for 1-12 hours.

Process B1

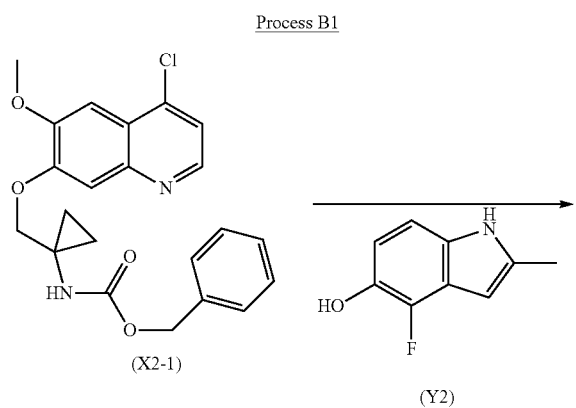

(X2-1)

(Y2)

Process B2

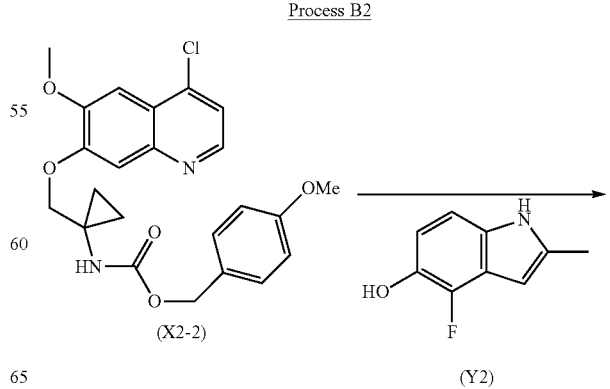

(X2-2)

(Y2)

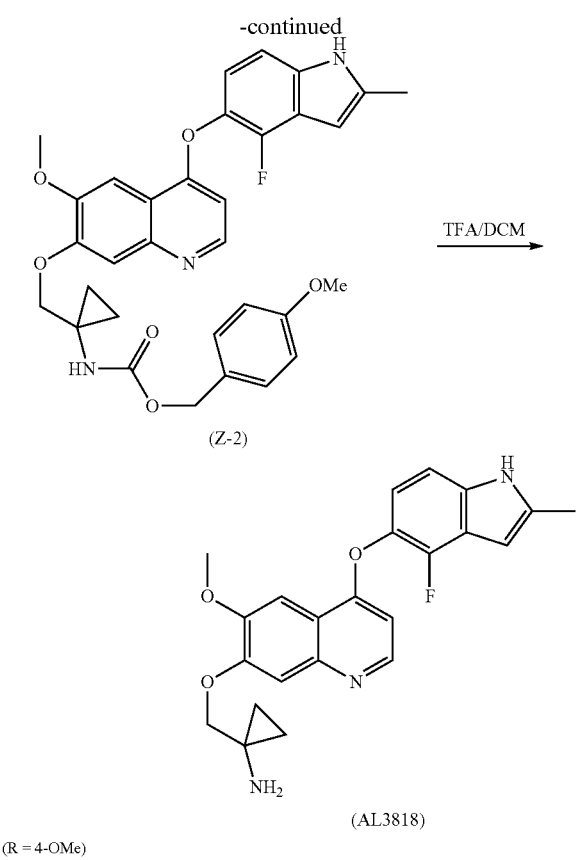

The following examples further illustrate the present invention, but should not be construed as in any way to limit its scope.

Example 1

Representation of Process A, Process A1

Process for Preparation of 1-((4-(4-Fluoro-2-methyl-1H-indol-5-yloxy)-6-methoxy-quinolin-7-yloxy)methyl)cyclopropanamine (AL3818)

To a stirred mixture of benzyl 1-(hydroxymethyl)cyclopropylcarbamate (50 g) and DCM (200 ml) was added DIPEA (39 g). The result solution was cooled to 0-5° C. with ice/water and further stirred under this temperature for 15 min. MsCl (30 g) was added via an addition funnel dropwise keeping temperature below 5° C. for about 1.5 hours. After completion of addition, the reaction mixture was allowed stirring at 0-5° C. for 30 min and quenched with saturated NaHCO₃ (150 ml). The solution was extracted with 150 ml DCM twice. The combined DCM layer was washed with 0.1 N HCl (400 ml) followed by brine. It was dried over Na₂SO₄ and concentrated to obtain an off-white solid 60 gram as (1-(benzyloxycarbonylamino)cyclopropyl)methyl methanesulfonate (Y1-1), MS: (M+1) 300.

To a stirred mixture of (Y1-1) (16 g), X1 [(4-(4-fluoro-2-methyl-1H-indol-5-yloxy)-6-methoxy-7-hydroxyquinoline, 12 g], K₂CO₃ (21 g) and KI (21 g) was added DMF (100 ml), the reaction suspension was heated at 80° C. for 10 hours and (Y1-1) (10 g) was added to continuously heated 80° C. for 10 hours. The reaction then was quenched with water (150 ml) and extracted with 150 ml DCM twice. The combined DCM layer was washed with 2 N NaOH (100 ml) followed by water and brine. It was dried over Na₂SO₄ and concentrated, further recrystallized from EtOH to obtain a yellow solid as benzyl 1-((4-(4-fluoro-2-methyl-1H-indol-5-yloxy)-6-methoxyquinolin-7-yloxy)methyl)cyclopropylcarbamate (Z-1) 9.5 g. MS: (M+1) 542.

To a stirred mixture of (Z-1) (9.5 g), HCOONH₄ (4.7 g) and Pd/C (10%, wet 50%, 4.7 g) was added MeOH, the reaction mixture was heated at 45° C. for 1.5 hours. It was then cooled and filtered through Celite, further evaporated. 2N HCl (200 ml) was added and extracted with DCM/MeOH (10/1, 100 ml) twice. The aqueous layer was basified with 3N NaOH to adjust pH 11-12 to generate a solid precipitation. The solid was filtered and washed with water to neutral, further suction dry. The solid was dissolved into a mixture of DCM/MeOH (250 ml, 10/1) and further washed with water and brine. It was dried with MgSO₄ and filtered, further evaporated to give a light yellow solid 5.5 g crude product. Further purification was conducted by dissolving the crude product into DCM/MeOH (40 ml, 10/1) to triturate with petroleum ether (40 ml) for 2 hours slow stirring. The precipitate was filtered and dried in an oven to give the final crystalline product 4.4 g (MP: 203-208° C.) and it can be further purified by recrystallizing from EtOH to give purer final product as a same crystalline form. MS: (M+1) 408; ¹H NMR (DMSO-d₆) δ 0.60-0.63 (d, 4H), 2.41 (s, 1H), 2.42-2.51 (t, 2H), 3.31 (s, 2H), 3.96 (s, 3H), 4.04 (s, 2H), 6.27 (s, 1H), 6.31-6.32 (m, 1H), 6.97-7.02 (t, 1H), 7.20-7.22 (d, 1H), 7.36 (s, 1H), 7.60 (s, 1H), 8.40-8.42 (d, 1H), 11.41 (s, 1H). MP: 208-210° C.; DSC Melting Range (Endo): 207-220° C. with Peak Temp=216° C. TGA demonstrating as an unsolvated material with weight loss at about 210° C. (between 205-215° C.). XRPD having pattern comprimising characteristic 10 peaks with intensity % greater than 10% expressed in d values and angles as follows:

| Angle | d value |
| --- | --- |
| 13.344 | 6.62986 |
| 15.858 | 5.58405 |
| 16.799 | 5.27326 |
| 17.640 | 5.02377 |
| 18.770 | 4.72373 |
| 20.650 | 4.29771 |
| 21.633 | 4.10463 |
| 23.087 | 3.84934 |
| 25.128 | 3.54112 |
| 26.607 | 3.34755 |

XRPD having pattern comprimising 26 characteristic peaks with all intensity % expressed in d values and angles as follows:

| NO. | Angle | d value | Intensity (%) |
| --- | --- | --- | --- |
| 1 | 10.892 | 8.11623 | 2.1 |
| 2 | 11.589 | 7.62991 | 6.1 |
| 3 | 12.195 | 7.25174 | 5.9 |
| 4 | 13.344 | 6.62986 | 36.2 |
| 5 | 15.858 | 5.58405 | 31.5 |
| 6 | 16.799 | 5.27326 | 77.9 |
| 7 | 17.640 | 5.02377 | 18.8 |
| 8 | 18.770 | 4.72373 | 11.9 |
| 9 | 19.987 | 4.43884 | 7.2 |
| 10 | 20.650 | 4.29771 | 42.0 |
| 11 | 21.633 | 4.10463 | 15.3 |
| 12 | 23.087 | 3.84934 | 100.0 |
| 13 | 24.356 | 3.65157 | 3.5 |

-continued

| NO. | Angle | d value | Intensity (%) |
|---|---|---|---|
| 14 | 25.128 | 3.54112 | 14.6 |
| 15 | 25.669 | 3.46768 | 3.8 |
| 16 | 26.607 | 3.34755 | 18.0 |
| 17 | 26.607 | 3.34755 | 3.1 |
| 18 | 29.050 | 3.07132 | 5.7 |
| 19 | 29.797 | 2.99602 | 1.5 |
| 20 | 30.681 | 2.91167 | 4.3 |
| 21 | 31.853 | 2.80718 | 1.2 |
| 22 | 33.524 | 2.67095 | 2.8 |
| 23 | 34.789 | 2.57667 | 2.6 |
| 24 | 35.873 | 2.50131 | 2.2 |
| 25 | 37.391 | 2.40313 | 3.9 |
| 26 | 38.637 | 2.32846 | 1.4 |

Figure 2:
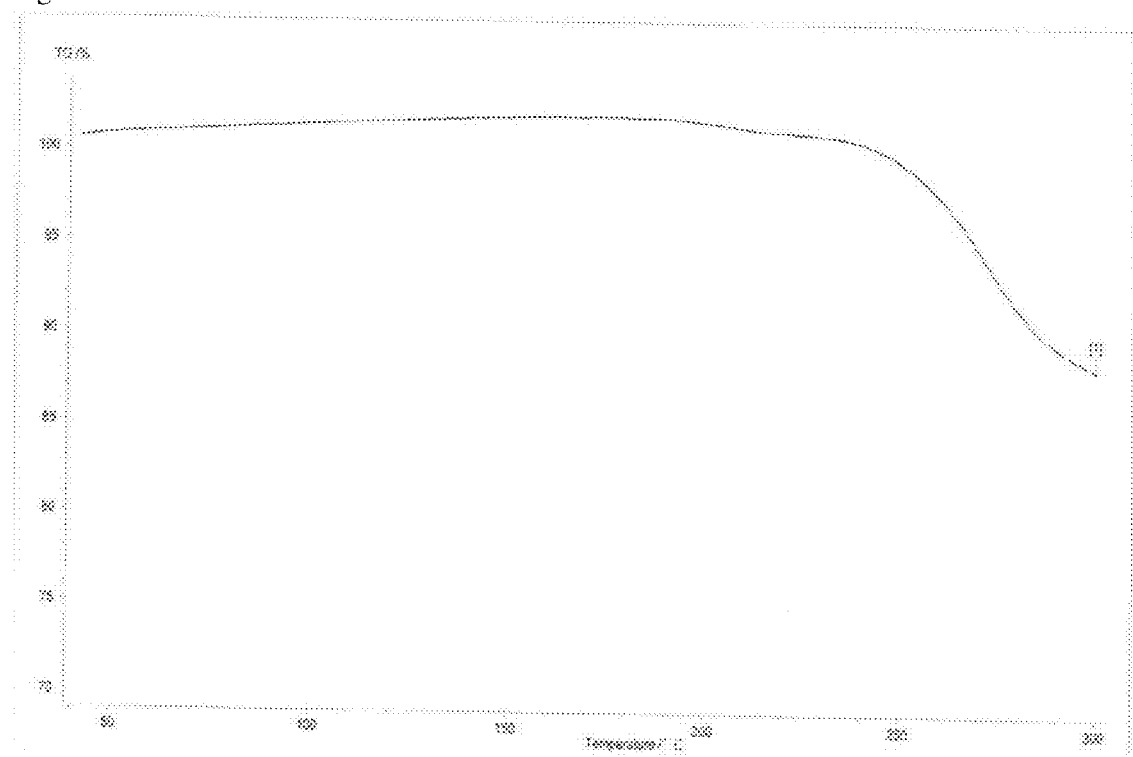
Figure 3:
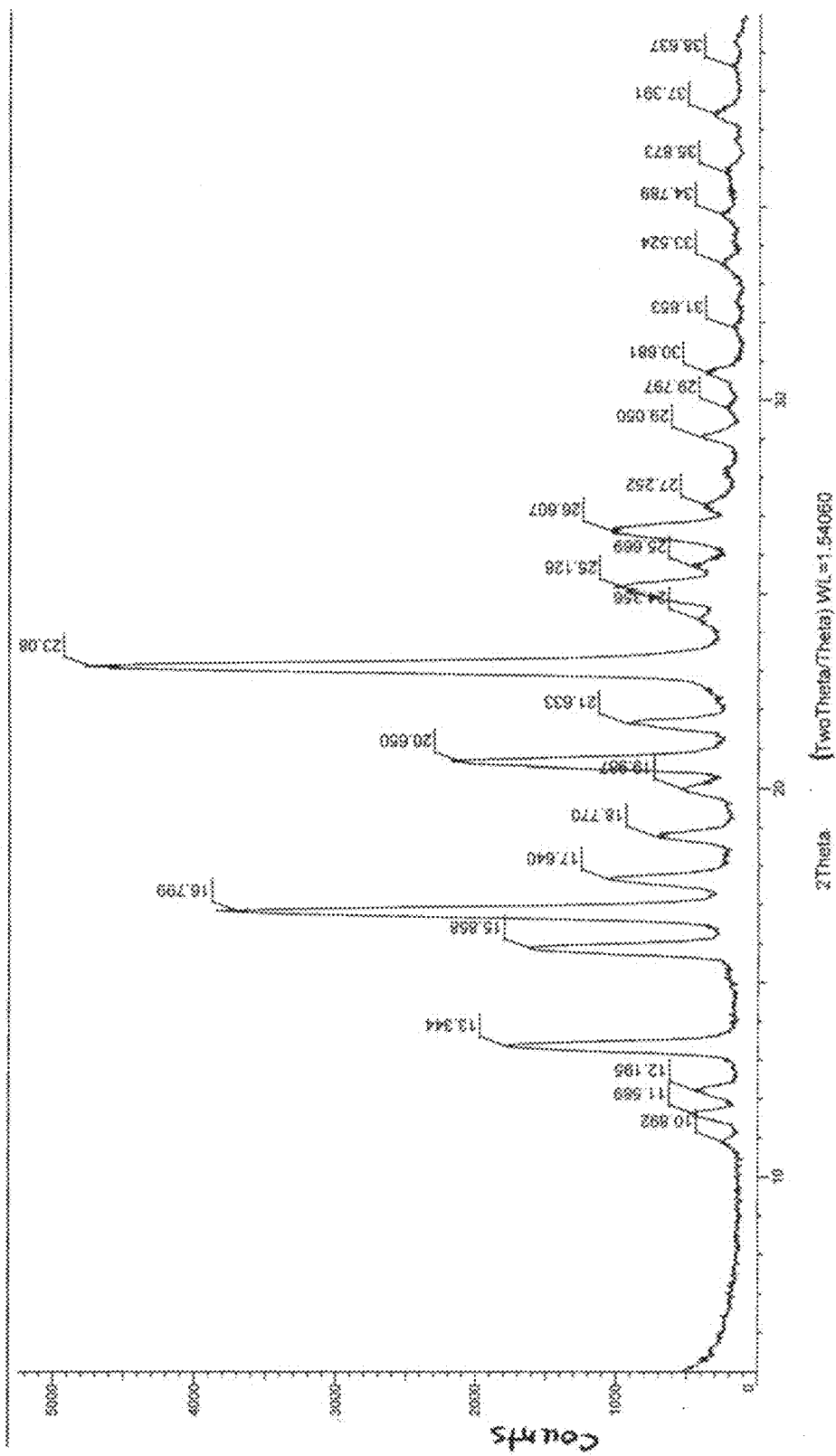

Graphs of DSC, TGA and XRPD are represented by FIG. 1, FIG. 2 and FIG. 3 respectively.

Example 2

Representation of Process A, Process A2

Process for Preparation of 1-((4-(4-Fluoro-2-methyl-1H-indol-5-yloxy)-6-methoxy-quinolin-7-yloxy)methyl)cyclopropanamine (AL3818)

It was similar prepared according to the preparation procedures of (Z-1) described in Example 1 by using 4-methoxybenzyl 1-(hydroxymethyl)cyclopropylcarbamate to first generate (1-((4-methoxybenzyloxy)carbonylamino)cyclopropyl)methyl methanesulfonate (Y1-2) then to give 4-methoxybenzyl 1-((4-(4-fluoro-2-methyl-1H-indol-5-yloxy)-6-methoxyquinolin-7-yloxy)-methyl)cyclopropyl-carbamate (Z-2), MS: (M+1) 572

To a stirred mixture of (Z-2) (1.5 g) in DCM (15 ml) at 0° C. was added TFA (1.5 ml) for about 30 min and warmed up to RT. The reaction was stirred at RT for 2 hours and added into water (30 ml). The aqueous layer was extracted with DCM twice (100 ml×2) and basified with 2N NaOH to adjust pH 11-12. The mixture was extracted with DCM (100 ml×3) and further washed with brine (100 ml). It was dried with $MgSO_4$ and filtered. The solution was evaporated to give 1.05 g crude final product. Further purification was conducted to dissolve the crude product into DCM/MeOH and triturated with petroleum ether and dried in an oven to give the final pure product 0.8 g AL3818 with the same crystalline form.

Example 3

Representation of Process A, Process B1

Process for Preparation of 1-((4-(4-Fluoro-2-methyl-1H-indol-5-yloxy)-6-methoxy-quinolin-7-yloxy)methyl)cyclopropanamine (AL3818)

To a mixture of benzyl 1-((4-chloro-6-methoxyquinolin-7-yloxy)methyl)cyclopropyl-carbamate (X2-1) (5 g), 4-fluoro-2-methyl-1H-indol-5-ol (Y2) (5 g) and DMAP (4 g) was added 1,6-lutidine (15 ml). The reaction was stirred and heated at 135° C. for 5 hours and was cooled followed by adding IPA with slow stirring for 2 hours at RT. The solid was filtered and further washed with IPA, dried to give (Z-1) 5.2 g as a solid. It was then similarly prepared according to deprotection procedures described of (Z-1) in Example 1 to give the final compound AL3818 with the same crystalline form.

Example 4

Representation of Process A, Process B2

Process for Preparation of 1-((4-(4-Fluoro-2-methyl-1H-indol-5-yloxy)-6-methoxy-quinolin-7-yloxy)methyl)cyclopropanamine (AL3818)

(Z-2) was similarly prepared according to the procedures described in Example 3 by using 4-methoxybenzyl 1-((4-chloro-6-methoxyquinolin-7-yloxy)methyl)cyclopropylcarbamate (X2-2) and (Y2). It was then similarly prepared according to deprotection procedures of (Z-2) described in Example 2 to give the final compound AL3818 with the same crystalline form.

Example 5

Preparation of 1-((4-(4-Fluoro-2-methyl-1H-indol-5-yloxy)-6-methoxy-quinolin-7-yloxy)-methyl)cyclopropanamine bishydrochloride acid salt and its crystalline To a 25 ml flask was added 250 mg free base (AL3818), 4N HCl in dioxane 0.625 mL (2.5 mmol, 4 eq.) in 10 ml EtOH, the reaction was heated at 75° C. for 30 minutes, cooled to RT and stirred for O.N. The solid was filtered and rinsed with acetone twice. It was dried in oven at 50° C. for 4 hours to give 126 mg white solid as the bishydrochloride salt as a crystalline and further recrystallized from EtOH to give a purer product as a same crystalline form. $^1$H NMR (DMSO-$d_6$) δ 1.09-1.24 (m, 4H), 2.43 (s, 3H), 4.08 (s, 3H), 4.40 (s, 2H), 6.32 (s, 1H), 6.76 (s, 1H), 7.05-7.11 (t, 1H), 7.27-7.30 (d, 1H), 7.65 (s, 1H), 7.82 (s, 1H), 8.64 (s, 2H), 8.70-8.73 (m, 1H), 11.51 (s, 1H). Chloride ion chromatography showed 2 molecular ratio ions. DSC Melting Range (Exo): 249-280 with Peak Temp=268° C. TGA demonstrating as an unsolvated material with weight loss at about 230° C. (between 225-235° C.). XRPD having pattern compromising 21 characteristic peaks with intensity % greater than 10% or 27 peaks with all intensity % expressed in d values and angles as follows:

| NO. | Angle | d value | Intensity (%) |
|---|---|---|---|
| 1 | 7.640 | 11.56173 | 19.5 |
| 2 | 8.642 | 10.22328 | 20 |
| 3 | 9.361 | 9.43969 | 13.3 |
| 4 | 10.091 | 8.75881 | 100.0 |
| 5 | 13.740 | 6.43957 | 26.4 |
| 6 | 14.479 | 6.11252 | 54.7 |
| 7 | 15.186 | 5.82962 | 10.1 |
| 8 | 15.766 | 5.61643 | 20.3 |
| 9 | 17.206 | 5.14957 | 7.4 |
| 10 | 18.569 | 4.77448 | 18.6 |
| 11 | 19.271 | 4.60215 | 11.0 |
| 12 | 20.041 | 4.42696 | 49.5 |
| 13 | 22.211 | 3.99909 | 58.4 |
| 14 | 22.814 | 3.89483 | 11.2 |
| 15 | 23.398 | 3.79886 | 11.6 |
| 16 | 24.455 | 3.63702 | 76.6 |
| 17 | 25.524 | 3.48708 | 34.6 |
| 18 | 26.703 | 3.33576 | 21.7 |
| 19 | 27.337 | 3.25978 | 18.4 |

-continued

| NO. | Angle | d value | Intensity (%) |
|---|---|---|---|
| 20 | 28.061 | 3.17732 | 18.5 |
| 21 | 28.801 | 3.09732 | 6.3 |
| 22 | 29.845 | 2.99133 | 13.8 |
| 23 | 31.331 | 2.85271 | 7.1 |
| 24 | 31.621 | 2.82721 | 9.5 |
| 25 | 32.840 | 2.72504 | 10.5 |
| 26 | 33.714 | 2.65632 | 3.8 |
| 27 | 38.348 | 2.34534 | 9.6 |

Figure 4:
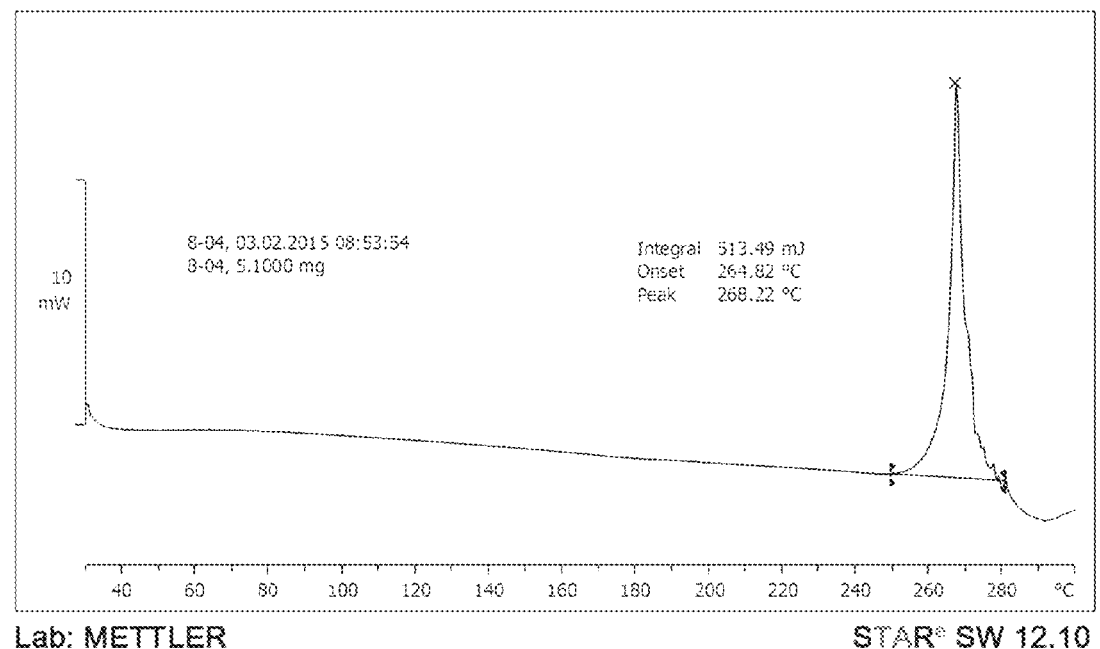
Figure 5:
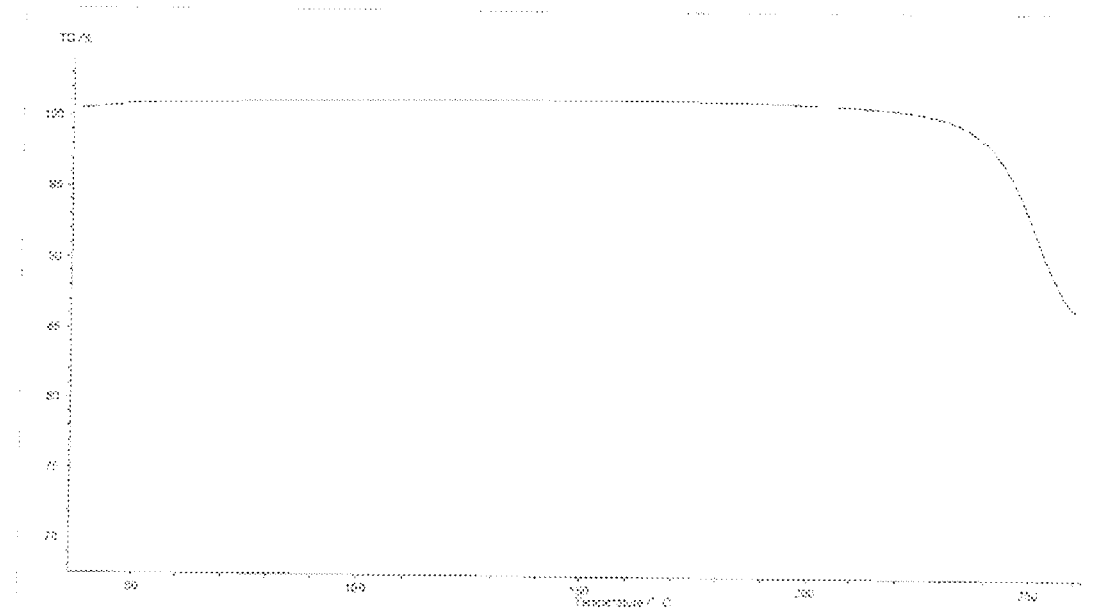
Figure 6:
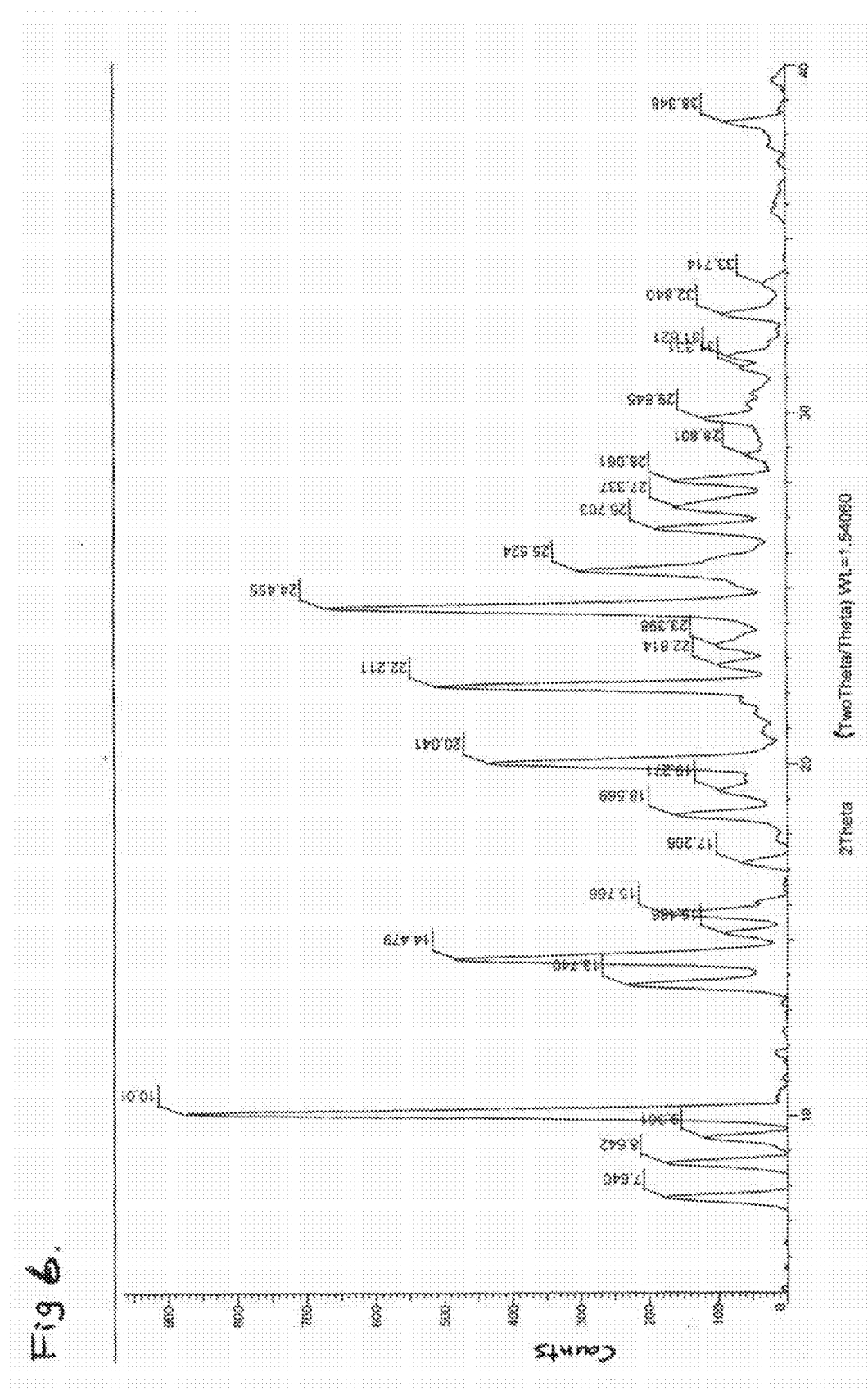

Graphs of DSC, TGA and XRPD are represented by FIG. 4, FIG. 5 and FIG. 6 respectively.

Example 6

Preparation of 1-((4-(4-Fluoro-2-methyl-1H-indol-5-yloxy)-6-methoxy-quinolin-7-yloxy)methyl)cyclopropanamine bishydrochloridehydrate acid salt and its crystalline To a 10 mL flask, charged 140 mg of 3818-2HCl salt from above Example 4 and 0.7 mL (×5 with salt volume) of 80% MeOH in H$_2$O. The result suspension was heated to 70° C. to form a solution and cooled to RT and further stirred for O.N. The solid was filtered and rinsed with acetone twice. It was dried in oven at 50° C. for 4 hours to obtain off-white solid 110 mg as the crystalline bishydrochloride hydrate salt. $^1$H NMR (DMSO-d$_6$) δ 1.09 (s, 2H), 1.22 (s, 2H), 2.44 (s, 1H), 2.52 (s, 2H), 4.09 (s, 3H), 4.44 (s, 2H), 6.32 (s, 1H), 6.81-6.82 (d, 1H), 7.08-7.14 (t, 1H), 7.29-7.32 (d, 1H), 7.79 (s, 1H), 7.85 (s, 1H), 8.75-8.78 (d, 1H), 8.85 (s, 2H), 11.66 (s, 1H). Chloride ion chromatography showed 2 molecular ratio ions. DSC Melting Range (Exo): 207-260° C. with Peak Temp=226° C. TGA demonstrating 2.68% (~3%, 1 water) weight loss till 120° C. (between 115-125° C.) and further weight loss at about 170° C. (between 165-175° C.). XRPD having pattern compromising 9 characteristic peaks with intensity % greater than 10% or 12 peaks with all intensity % expressed in d values and angles as follows:

| NO. | Angle | d value | Intensity (%) |
|---|---|---|---|
| 1 | 5.506 | 16.03679 | 28.0 |
| 2 | 6.817 | 12.95694 | 100 |
| 3 | 8.087 | 10.92445 | 29.9 |
| 4 | 9.766 | 9.04936 | 20.6 |
| 5 | 13.318 | 6.64283 | 22.3 |
| 6 | 14.332 | 6.17523 | 7.0 |
| 7 | 16.159 | 5.48067 | 15.7 |
| 8 | 19.474 | 4.55451 | 8.8 |
| 9 | 20.920 | 4.24296 | 6.5 |
| 10 | 20.920 | 3.87231 | 28.2 |
| 11 | 25.087 | 3.54678 | 20.2 |
| 12 | 25.874 | 3.44064 | 22.7 |

Figure 7:
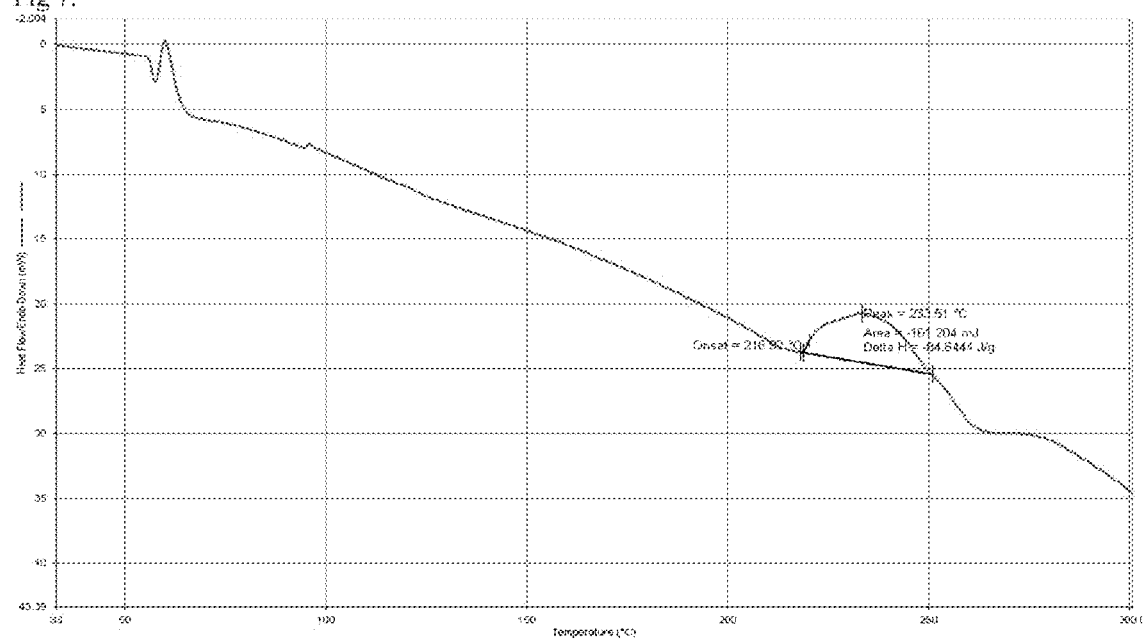
Figure 8:
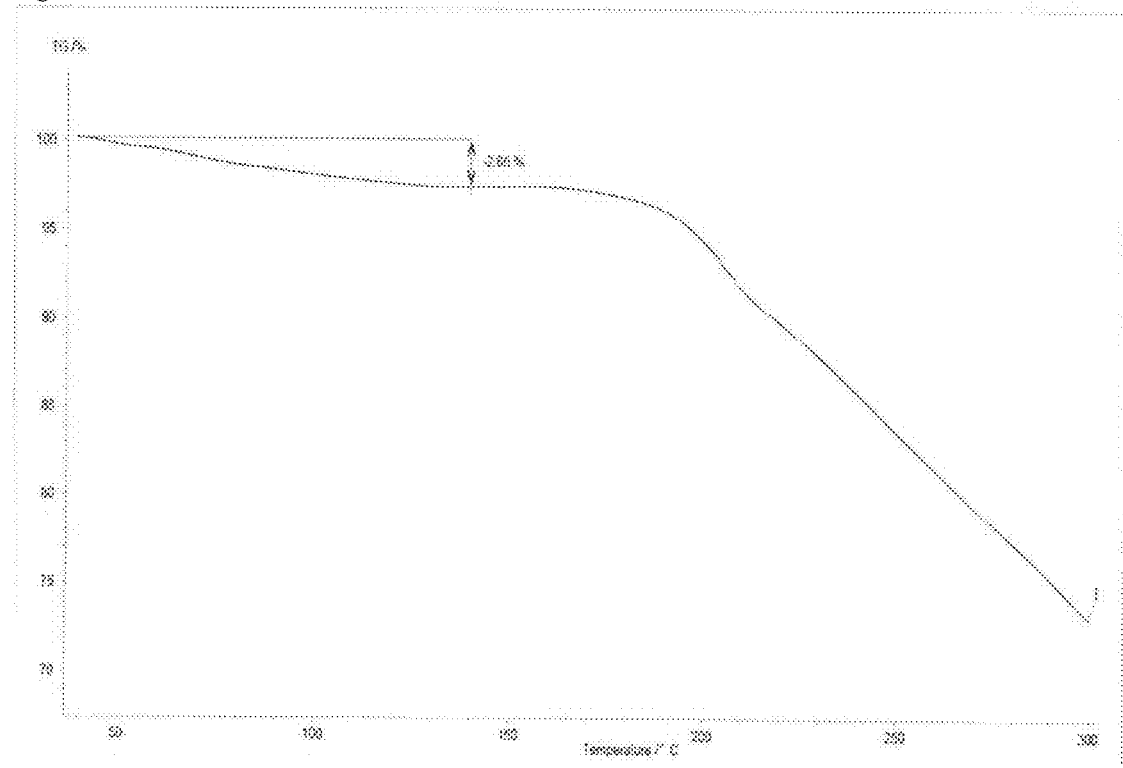
Figure 9:
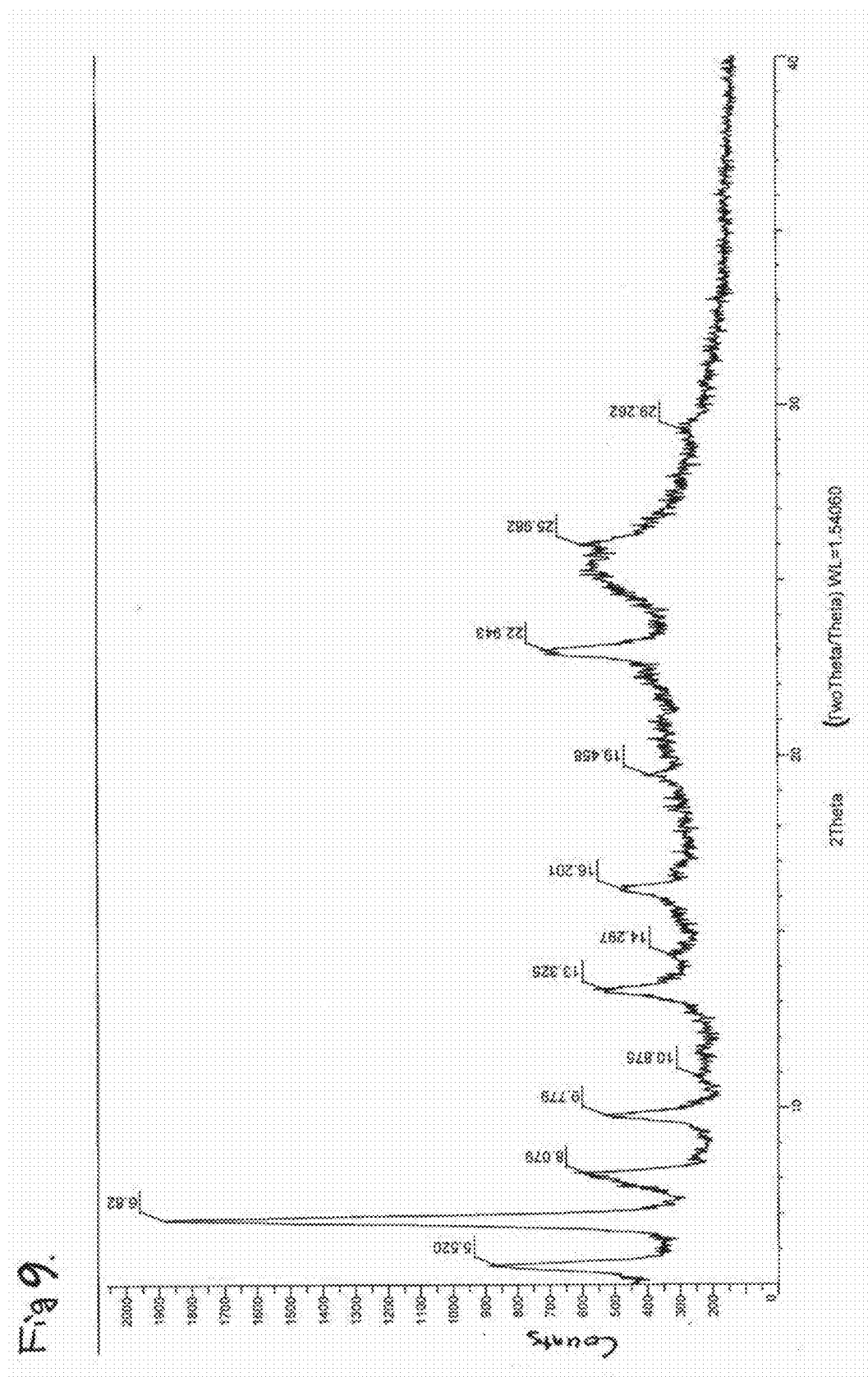

Graphs of DSC, TGA and XRPD are represented by FIG. 7, FIG. 8 and FIG. 9 respectively.

Example 7

Preparation of 1-((4-(4-Fluoro-2-methyl-H-indol-5-yloxy)-6-methoxy-quinolin-7-yloxy)-methyl)cyclopropanamine bismaleic acid salt and its crystalline To a 25 mL flask was added 50 mg free base (AL3818) in 1.5 mL EtOH, the reaction was heated to 70° C. with stirring. To the result solution was added 36 mg (2.5 eq) maleic acid as solid and stirred at 70° C. for 0.5 hr. It was cooled to RT and stirred for O.N. The solid was filtered and rinsed with acetone twice further dried in oven at 50° C. for 4 hours to obtain 68 mg of as a crystalline solid and further recrystallized from EtOH to give a purer product as a same crystalline form as two (bis) maleic acid salt. $^1$H NMR (DMSO-d$_6$) δ 0.73 (s, 2H), 0.88 (s, 2H), 3.43 (s, 2H), 3.53 (s, 2H), 3.59 (s, 2H), 3.86 (s, 4H), 3.97 (s, 3H), 4.41 (s, 1H), 6.07 (s, 2H), 7.26 (s, 1H), 7.44-7.50 (t, 1H), 7.76-7.79 (d, 1H), 7.88 (s, 1H), 8.10-8.12 (d, 1H), 8.55 (s, 1H), 9.54 (s. 1H). Maleic ion chromatography showed 2 molecular ratio ions. DSC Melting Range (Endo): 165-202° C. with Peak Temp=183° C. TGA demonstrating as an unsolvated material with weight loss at about 160° C. (between 155-165° C.). XRPD having pattern compromising 22 characteristic peaks with intensity % greater than 10% or 35 peaks with all intensity % expressed in d values and angles as follows:

| NO. | Angle | d value | Intensity (%) |
|---|---|---|---|
| 1 | 6.716 | 13.14986 | 29.7 |
| 2 | 8.816 | 10.02189 | 34.3 |
| 3 | 9.743 | 9.07069 | 15.3 |
| 4 | 10.033 | 8.80923 | 21.4 |
| 5 | 11.777 | 7.50803 | 21.2 |
| 6 | 13.418 | 6.59342 | 6.2 |
| 7 | 14.816 | 5.97445 | 11.0 |
| 8 | 16.089 | 5.50434 | 9.5 |
| 9 | 16.801 | 5.27279 | 24.5 |
| 10 | 17.360 | 5.10409 | 87.9 |
| 11 | 17.179 | 5.15755 | 70.7 |
| 12 | 18.190 | 4.87308 | 20.2 |
| 13 | 18.704 | 4.74028 | 16.7 |
| 14 | 19.296 | 4.59623 | 5.0 |
| 15 | 19.920 | 4.45371 | 12.6 |
| 16 | 20.824 | 4.26227 | 65.5 |
| 17 | 21.457 | 4.13785 | 100.0 |
| 18 | 22.411 | 3.96393 | 4.5 |
| 19 | 22.876 | 3.88434 | 5.8 |
| 20 | 23.204 | 3.83021 | 19.0 |
| 21 | 23.622 | 3.76332 | 78.4 |
| 22 | 24.418 | 3.64247 | 6.3 |
| 23 | 26.140 | 3.40621 | 87.0 |
| 24 | 26.958 | 3.30469 | 26.5 |
| 25 | 27.383 | 3.25443 | 61.3 |
| 26 | 28.154 | 3.16697 | 41.5 |
| 27 | 29.554 | 3.02013 | 6.8 |
| 28 | 30.611 | 2.91815 | 23.7 |
| 29 | 31.373 | 2.84906 | 14.3 |
| 30 | 33.457 | 2.67620 | 6.7 |
| 31 | 34.541 | 2.59465 | 2.8 |
| 32 | 35.137 | 2.55199 | 3.8 |
| 33 | 35.734 | 2.51067 | 2.5 |
| 34 | 37.129 | 2.41949 | 8.6 |
| 35 | 39.704 | 2.26833 | 3.9 |

Figure 10:
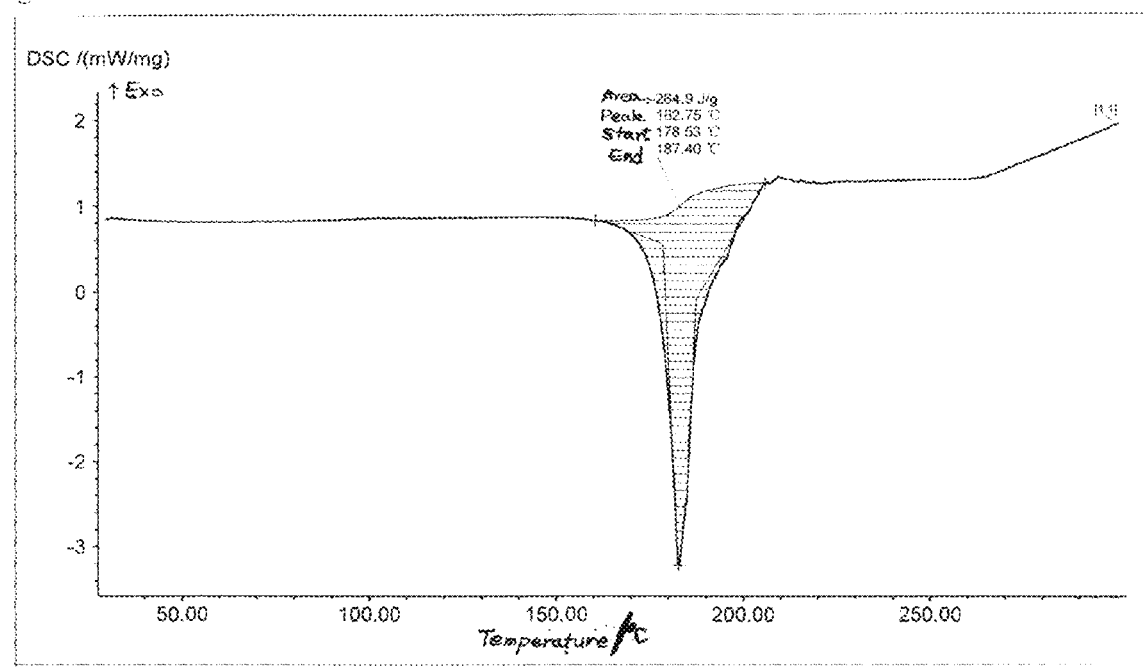
Figure 11:
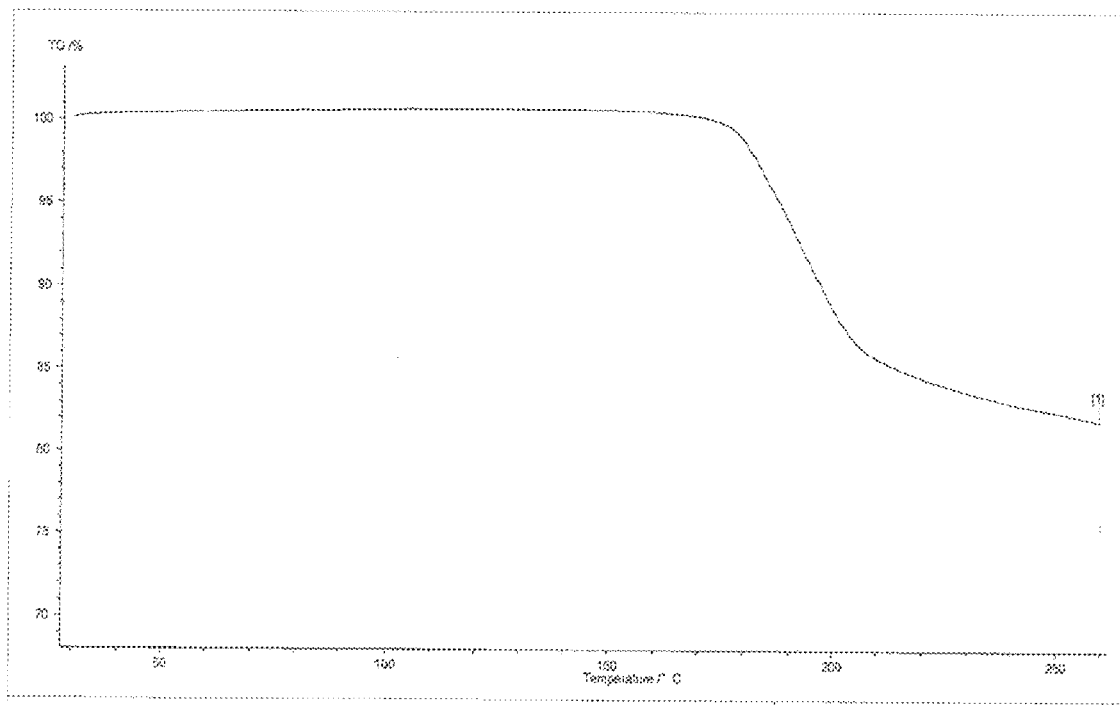
Figure 12:
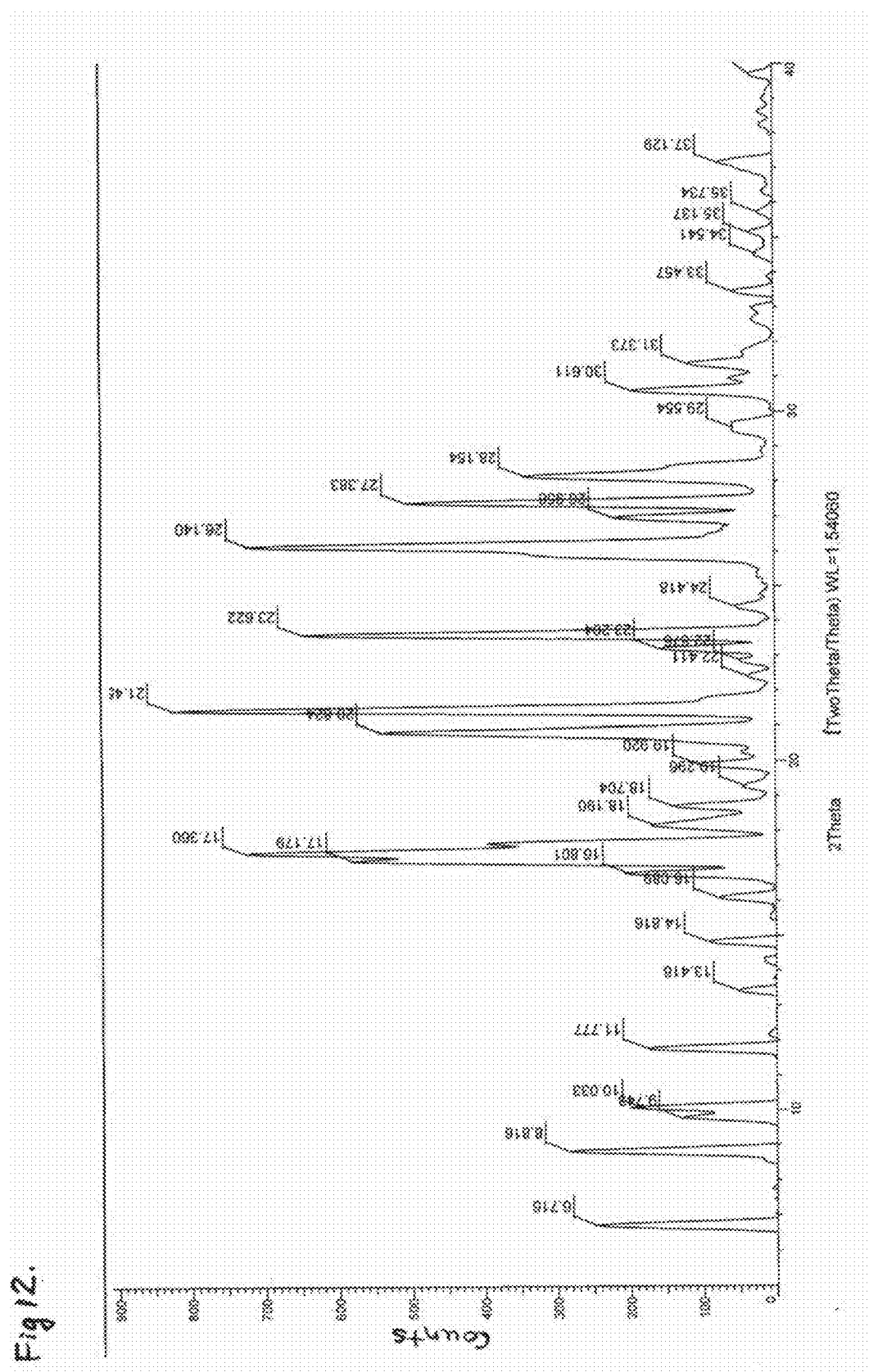

Graphs of DSC, TGA and XRPD are represented by FIG. 10, FIG. 11 and FIG. 12 respectively.

Example 8

Preparation of 1-((4-(4-Fluoro-2-methyl-H-indol-5-yloxy)-6-methoxy-quinolin-7-yloxy)methyl)cyclopropanamine succinic acid salt and its crystalline To a 50 mL flask was added 100 mg free base (AL3818) in 4 mL EtOH, the reaction was heated to 75° C. with stirring. To the result solution was added succinic acid as solid 36 mg (0.308 mmol, 1.25 eq) and stirred at 75° C. for 0.5 hr. It was cooled to RT and stirred for overnight. The solid was filtered and rinsed with acetone twice further dried in oven at 50° C. for 4 hours to obtain a crystalline solid 84 mg and further recrystallized from EtOH to give a purer product as a same crystalline form. $^1$H NMR (DMSO-d$_6$) δ 0.72 (s, 4H), 2.37-2.42 (m, 7H), 3.99 (s, 3H), 4.10 (s, 2H), 6.27 (s, 1H), 6.32-6.33 (d, 1H), 6.97-7.02 (t, 1H), 7.20-7.23 (d, 1H), 7.39 (s, 1H), 7.61 (s, 1N), 8.42 (s, 2H), 11.41 (s, 1H). Succnic ion chromatography showed 1 molecular ratio ions. DSC Melting Range: Melting Range (Endo): 176-202° C. with Peak Temp=198° C. TGA demonstrating as an unsolvated material with weight loss at about 180° C. (between 175-185° C.). XRPD having pattern compromising 11 characteristic peaks with intensity % greater than 10% or 19 peaks with all intensity %:

| NO. | Angle | d value | Intensity (%) |
|---|---|---|---|
| 1 | 5.765 | 15.31849 | 12.9 |
| 2 | 8.038 | 10.98994 | 7.4 |
| 3 | 11.639 | 7.59700 | 27.7 |
| 4 | 12.9506 | 6.83065 | 100 |
| 5 | 16.1415 | 5.48683 | 18.0 |
| 6 | 17.4835 | 5.06846 | 18.7 |
| 7 | 18.385 | 4.82175 | 17.8 |
| 8 | 19.394 | 4.57325 | 1.1 |
| 9 | 20.756 | 4.27609 | 13.4 |
| 10 | 22.034 | 4.03092 | 2.8 |
| 11 | 23.167 | 3.83630 | 1.8 |
| 12 | 24.085 | 3.69200 | 16.9 |
| 13 | 24.485 | 3.63268 | 14.6 |
| 14 | 25.737 | 3.45874 | 13.7 |
| 15 | 28.621 | 3.11637 | 6.4 |
| 16 | 29.255 | 3.05025 | 22.1 |
| 17 | 31.357 | 2.85048 | 0.9 |
| 18 | 31.967 | 2.79743 | 2.1 |
| 19 | 35.630 | 2.51780 | 2.4 |

Figure 13:
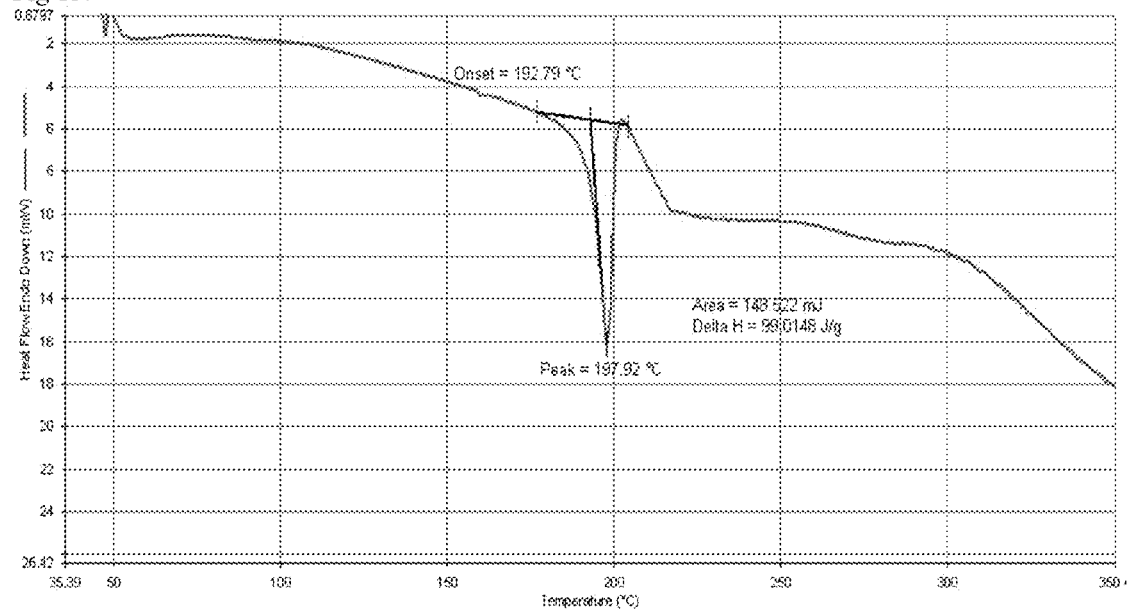
Figure 14:
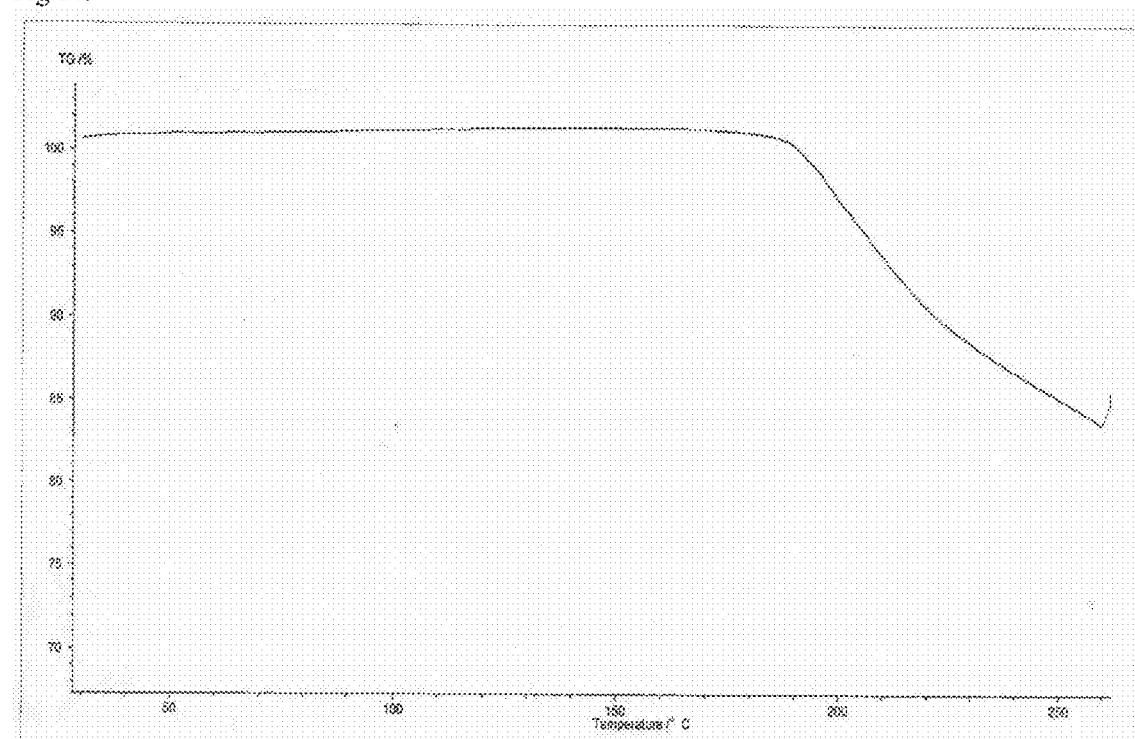
Figure 15:
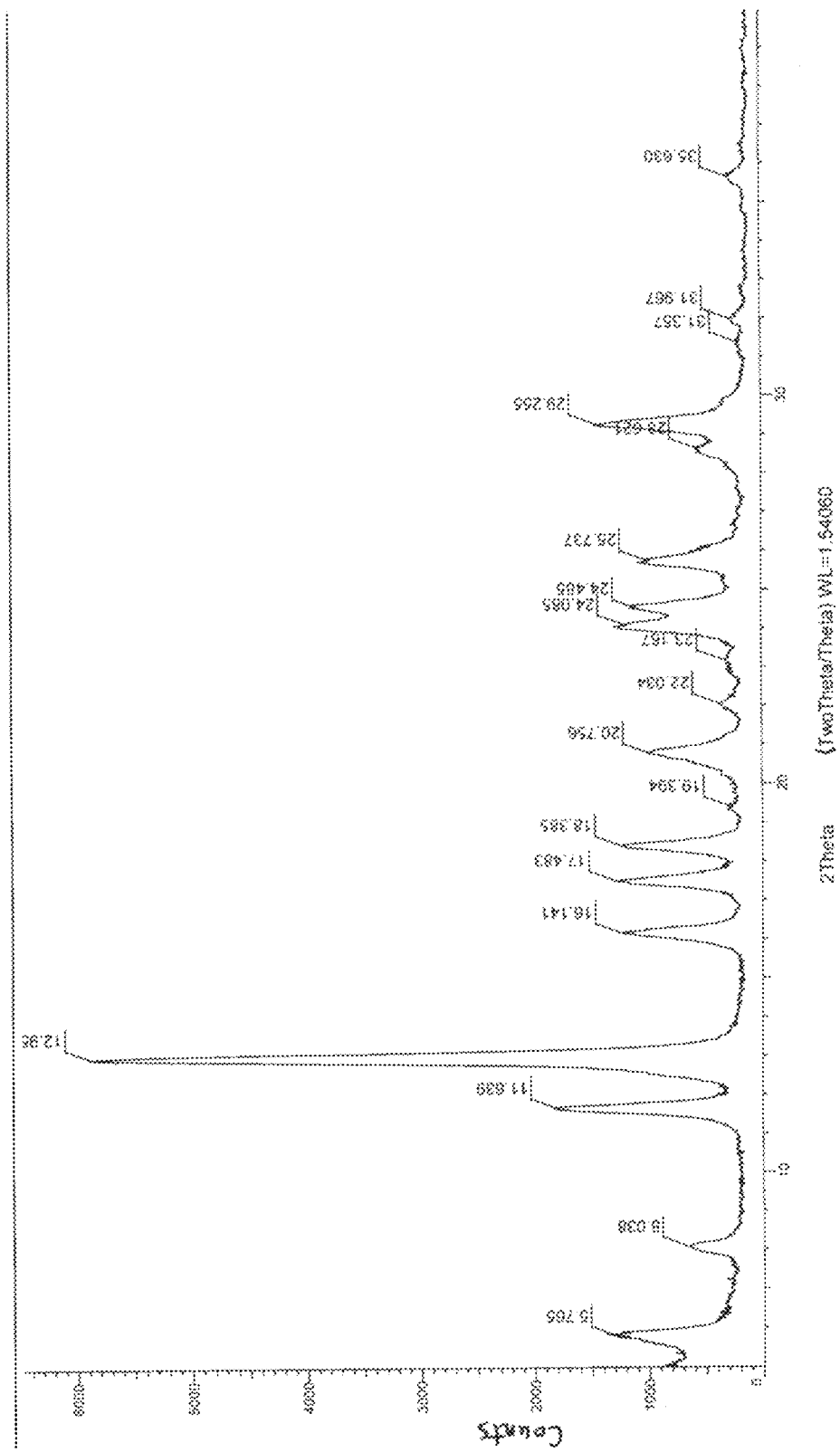

Graphs of DSC, TGA and XRPD are represented by FIG. 13, FIG. 14 and FIG. 15 respectively.

Example 9

In vitro MTT (proliferation) assay was performed with compound from above examples to give following inhibition results:

| | Sample Name | | | | |
|---|---|---|---|---|---|
| Cancer Cell Lines | AL3818-H1 (2HCl) IC50 (μM) | AL3818-H2 (2HCl•HCl) IC50 (μM) | AL3818-S (Succinic) IC50 (μM) | AL3818-M (Bismaleic) IC50 (μM) | AL3818-F (Free Base) IC50 (μM) |
| PANC-1 (pancreatic) | 1.58 | 1.55 | 1.24 | 1.15 | 1.34 |
| NC1-H157 (lung) | 7.18 | 2.29 | 2.28 | 2.02 | 1.83 |
| MDA-MB-231 (breast) | 10.25 | 5.71 | 6.1 | 5.37 | 5.56 |
| Hela (cervical) | 3.7 | 4.07 | 4.66 | 3.94 | 3.23 |
| PC-3 (prostate) | 5.53 | 3.88 | 4.41 | 3.62 | 5.11 |
| BEL7404 (liver) | 2.75 | 1.74 | 1.43 | 1.15 | 0.93 |
| MKN45 (gastric) | 1.77 | 3.9 | 4.16 | 2.65 | 3.11 |
| Ishikawa (endometrial) | 5.67 | 1.56 | 1.32 | 1.34 | 1.04 |
| Saos-2 (sarcoma) | 4.68 | 4.98 | 5.68 | 5.49 | 5.13 |
| SKOV3 (ovarian) | 5.34 | 5.7 | 7.6 | 6.56 | 5.97 |
| SW579 (thyroid) | 2.33 | 1.29 | 2.61 | 1.15 | 1 |
| HCT116 (colon) | 3.45 | 3.34 | 3.94 | 4.62 | 3.25 |

Example 10

Based on the inventor's research experience using AL3818 free base, its 2HCl salts, its bis-maleic acid salt and its succinic salt, the following tumor inhibition results are expected in a MTT assay according to Example 9.

2-10 μM±1.7 μM in vitro inhibition activities are expected on various solid tumor cell lines, such as renal, melanoma, head/neck, bladder, brain; and blood cancers, such as ALL, CLL, AML, CML and Multiple Myeloma.

Example 11

Animal antitumor activity in vivo testing with endometrial Ishikawa cell line (xenograft) is performed as follows:

The well grown tumor tissue of endometrial cancer Ishikawa was cut into 3 mm pieces, and each nude mouse was subcutaneously inoculated with one piece into the right armpit. The animals were grouped and administrated as following:

1) AL3818-H1 (Bishydrochloride acid salt, 2HCl), MW: 480, 3.54 mg/kg
2) AL3818-H2 (Bishydrochloridehydrate acid salt, 2HCl.H$_2$O), MW: 598, 3.67 mg/kg
3) AL3818-S(Succinic acid salt), MW: 525, 3.87 mg/kg
4) AL3818-M (Bismaleic acid salt), MW: 639, 4.71 mg/kg
5) AL3818-F (Free Base), MW: 407, 3 mg/kg
6) Control Treatments were initiated when the tumors size reached above 100 mm$^3$ after 13 days. According to the size of tumor, the animals with oversize or undersize tumors were eliminated, and the animals were grouped with similar average tumor volume. Then the animals were oral administrated daily for continuous 14 days with volume of 0.5 ml/20 g as the above. The large diameter a (mm) and the small diameter b (mm) were measured with caliper twice a week after inoculation for 13 days. The tumor volume was calculated by formular: TV=ab$^2$/2. The relative tumor volume was calculated as: RTV=Vt/Vo, Vo represents the tumor volume on the first day of treatment; Vt represents the tumor volume on each measurement day. The animals were executed and tumors were got by dissection 30 days after inoculation (D18). Then, the individual body weight and tumor weight were determined, and calculate as following formula.

Figure 16:
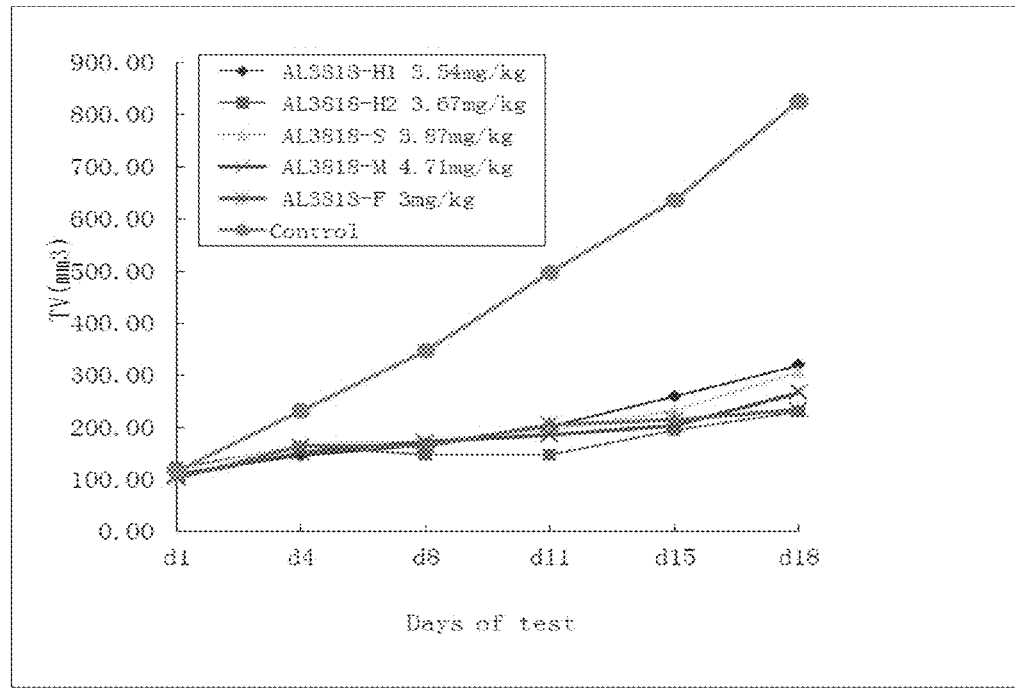
Figure 16:
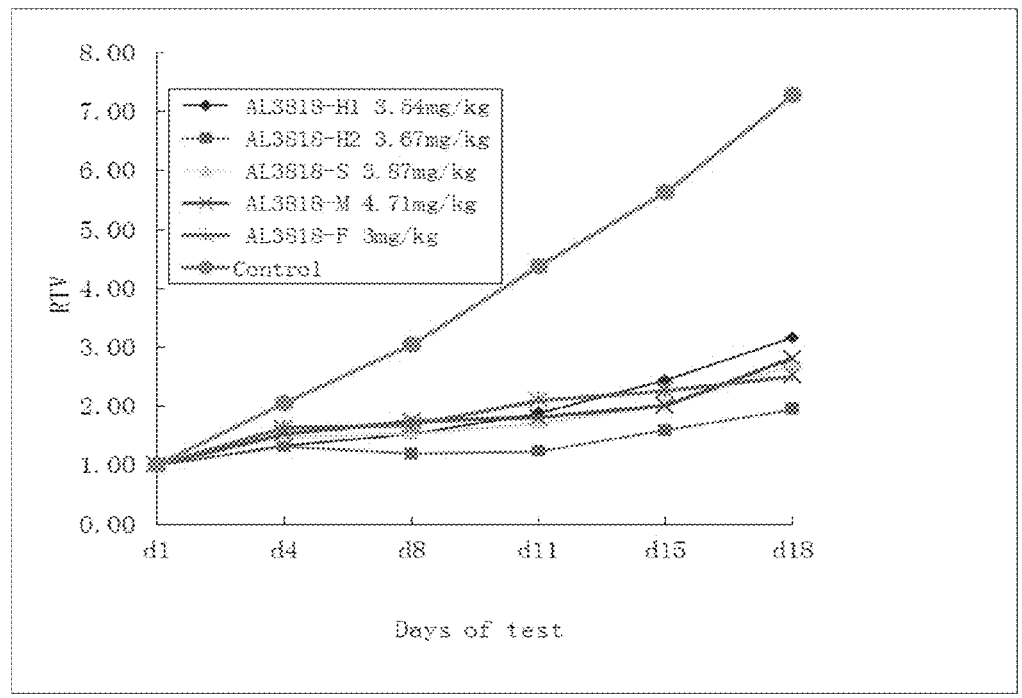

Tumor inhibition activities are between 50-95%. Results are shown in FIG. 16.

Example 12

Based on the inventor's research experience using AL3818 free base, its HCl salts (mono or bis), its bis-maleic acid salt and its succinic salt, the following in vivo tumor inhibition results (xenografts) are expected according to Example 11.

50%-100% in vivo tumor inhibition activities are expected on various solid tumor cell lines, such as lung, renal, colorectal, gastric, melanoma, head/neck, thyroid, pancreatic, liver, prostate, bladder, brain, sarcoma, breast, ovarian, cervical and endometrial cancers; and blood cancers, such as ALL, CLL, AML, CML and Multiple Myeloma.

Example 13

Figure 17:
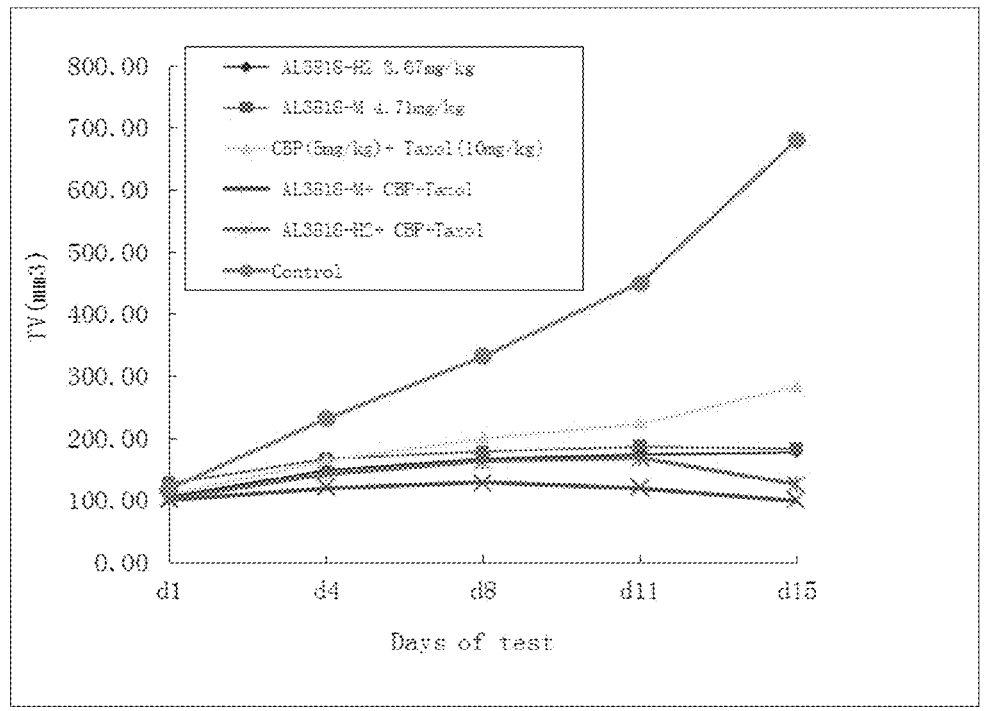
Figure 17:
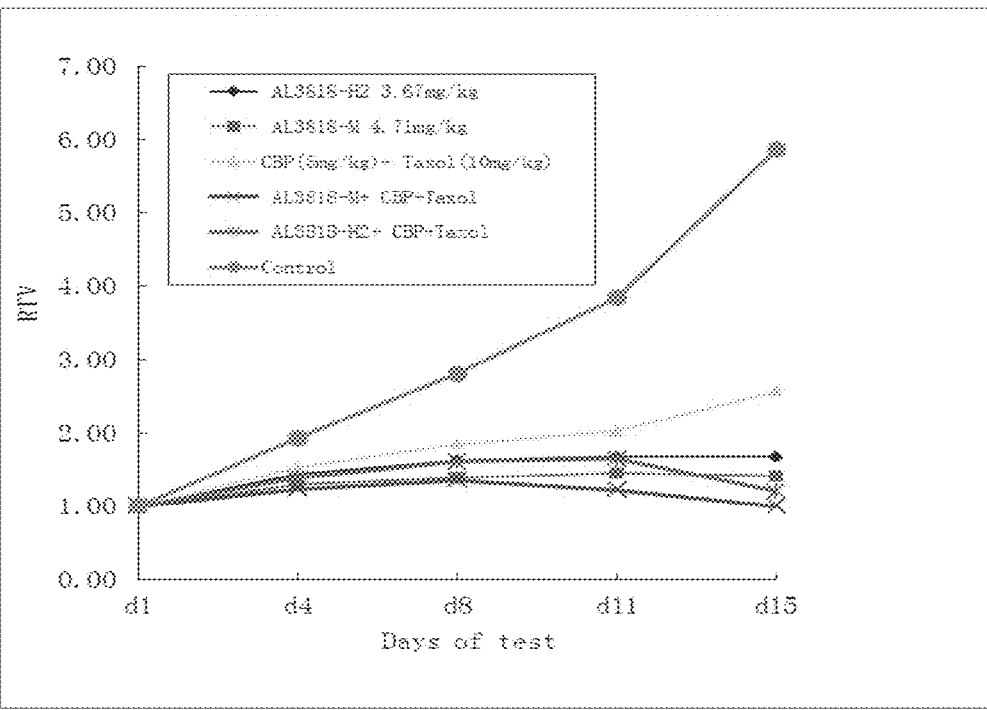

AL3818 bis HCl salt and bis-maleic acid salt were also tested in combining with chemotherapy by using platinum based, taxane based or both; such as: cisplatin, carboplatin, paclitaxel or cisplatin/paclitaxel, carboplatin/paclitaxel combined. The experiment of combination with carboplatin/paclitaxel was carried out similar to the description of Example 11. Tumor inhibition activities are between 50 to >100%. Results are shown in FIG. 17.

Example 14

Based on the inventor's research experience using AL3818 free base, its HCl salts (mono or bis), its bis-maleic acid salt and its succinic salt, the following in vivo combing chemotherapy (standard of care, such as platinum based, taxane based or both chemotherapy) tumor inhibition results (xenografts) are expected according to Example 13, especially combing with cisplatin, carboplatin, paclitaxel or cisplatin/paclitaxel, carboplatin/paclitaxel together.

50 to >100% regression in vivo tumor inhibition activities are expected on various solid tumor cell lines, such as lung, renal, colorectal, gastric, melanoma, head/neck, thyroid, pancreatic, liver, prostate, bladder, brain, sarcoma, breast, ovarian and cervical cancers; and blood cancers, such as ALL, CLL, AML, CML and Multiple Myeloma.

Example 15

| Sample Name | | | | |
|---|---|---|---|---|
| AL3818-H1 (2HCl) (mg/ml) | AL3818-H2 (2HCl·H2O) (mg/ml) | AL3818-S (Succinic) (mg/ml) | AL3818-M (2Maleic) (mg/ml) | AL3818-F (Free Base) (mg/ml) |
| water solubility 6 | 7 | 0.1 | 0.5 | 0.02 |

Water solubility of each salt and free base has been tested as well to give the following results:

Example 16

A Mouse Model of Laser-Induced Choroidal Neovascularization (CNV)

Figure 18:
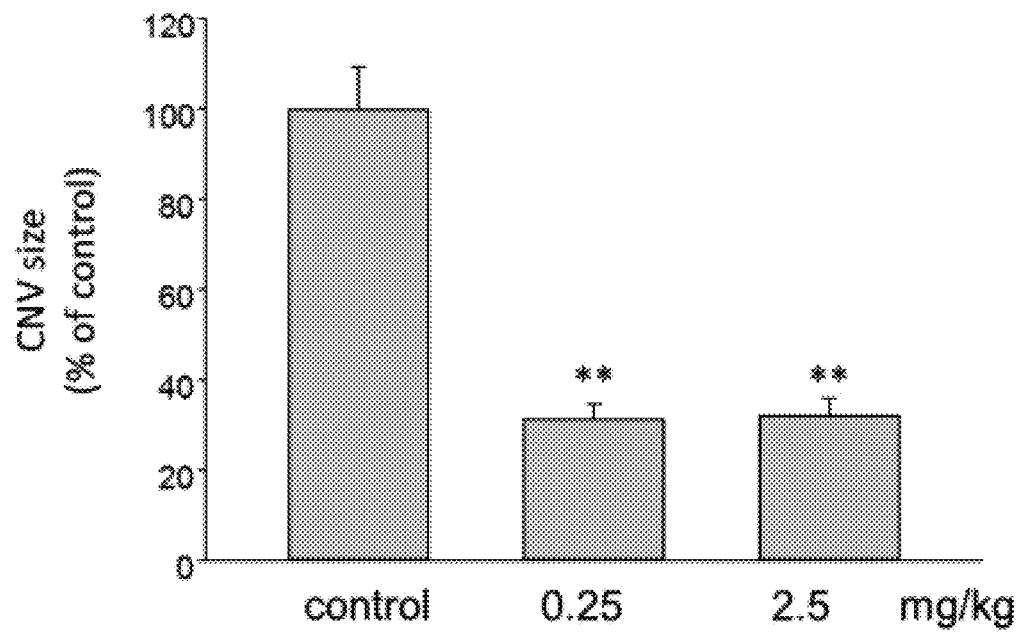

(1) Experiments were performed in C57 BL/6 mice at 10 to 12 weeks of age. Laser CNV was induced with a 532 nm diode laser mounted on a slit lamp, using 50 μm spot size, 100 ms duration and 100 mW laser energy. Each eye received 4 laser burns. Stock solution of AL3818-H1 was made by dissolving the compound in water to 25 mg/ml concentration, and further diluted to working solution of either 250 or 25 μg/ml in water. Mice were orally gavaged at dosage of 2.5 or 0.25 mg/kg body weight, in volume of 200 μl per 20 gram of body weight, once every day starting at one day before laser treatment until 10 days afterwards. Control group mice will receive gavage with water which is used to dissolve the compound. By the end of the experiment, mice were subjected to fluorescence angiography to exclude the spots with hemorrhage and other mechanic injuries caused by the procedures. Mice were sacrificed and CNV size was measured by immunostaining of RPE/choroid flat mount co-stained with FITC-conjugated isolectin B4 and anti-ICAM2 antibody. For groups of control, 0.25 mg/kg and 2.5 mg/kg, we examined 43, 44 and 49 eyes on RPE/choroid flat mount. After immunostaining, images were taken on a Zeiss fluorescence microscope. CNV size was measured in Image J software. Our results (FIG. 18) show that mice treated with AL3818 at 0.25 or 2.5 mg/kg body weight had nearly 70% reduction in average size of laser-induced CNV.

Figure 19:
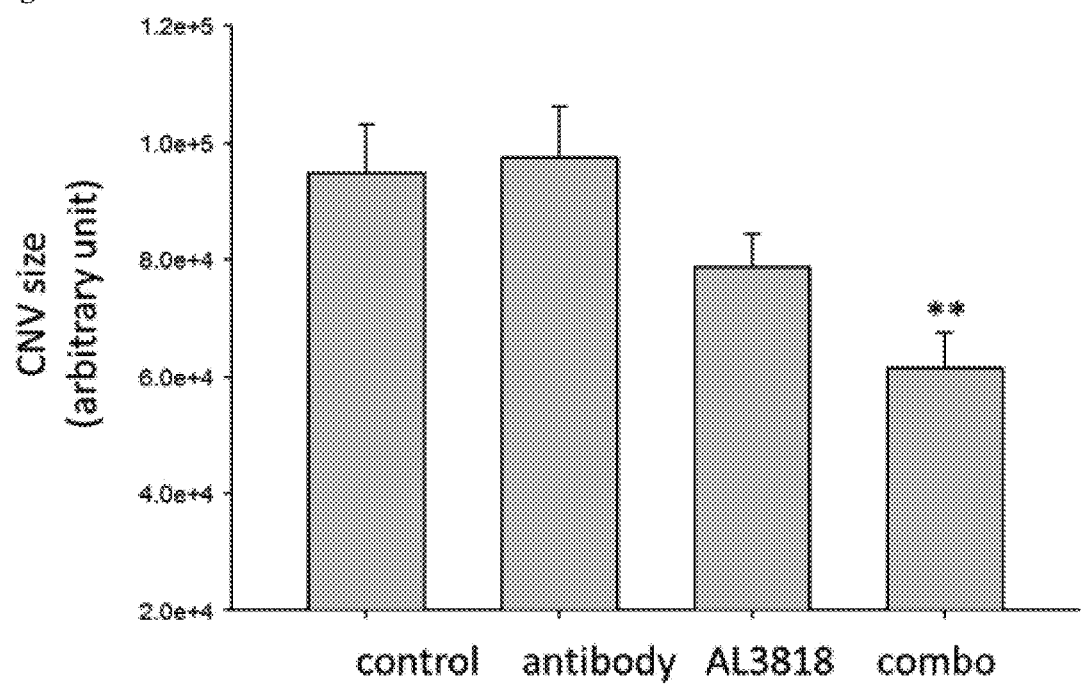

(2) The potential synergistic or additive effects between AL3818-M and anti-VEGF antibody was also studied. Immediately after laser burn, mice were treated with a monoclonal VEGF neutralizing antibody from R&D Systems (mAb AF564) at 1 μg dosage by intravitreal injection. We had 4 experimental groups: control (treated with water), AL3818-M, anti-VEGF, and AL3818-M+anti-VEGF. A total of 75 laser spots were analyzed. Mice in control or AL3818-M alone group received the intravitreal injection of saline in the same 2 μl volume. The results ((FIG. 19) showed that eyes treated with 0.15 mg/kg AL3818 and 1 pig anti-VEGF antibody had a nearly 30% reduction in laser CNV as compared to the control group (P<0.01, one-way ANOVA, Dunnett post-hoc test).

Example 17

Based on the inventor's research experience using AL3818 free base, its HCl salts (mono or bis), its bis-maleic acid salt and its succinic salt, in vivo animal model CNV efficacies which related to effective treatment of an optometric disease, such as AMD (Age-Related Macular Degeneration) but not limited, are definitely expected according to Example 16; or combing these compounds with anti-VEGF antibody or VEGF trap, such as ranibizumab or aflibercep but not limited, to generate a synergistic treatment effect are definitely expected according to Example 16 as well.

What is claimed is:

1. A crystalline form of 1-((4-(4-Fluoro-2-methyl-1H-indol-5-yloxy)-6-methoxyquino-lin-7-yloxy)methyl)cyclopropanamine of AL3818 exhibiting at least one of following characters:
    a melting point at 208° C.-210° C.;
    a DSC Melting Range (Endo): 207-220° C. with Peak Temp=216° C., pattern shown in FIG. 1;
    a TGA thermogram that doesn't exhibit significant weight loss until at 205-215° C., pattern shown in FIG. 2.

2. A crystalline form of 1-((4-(4-Fluoro-1-methyl-1H-indol-5-yloxy)-6-methoxyquino-lin-7-yloxy)methyl)cyclopropanamine according claim 1 exhibiting a XRPD having pattern shown in FIG. 3 comprising 10 characteristic peaks with intensity % greater than 10% expressed in d values and angles as follows:

| Angle | d value |
|---|---|
| 13.344 | 6.62986 |
| 15.858 | 5.58405 |
| 16.799 | 5.27326 |
| 17.640 | 5.02377 |
| 18.770 | 4.72373 |
| 20.650 | 4.29771 |

-continued

| Angle | d value |
|---|---|
| 21.633 | 4.10463 |
| 23.087 | 3.84934 |
| 25.128 | 3.54112 |
| 26.607 | 3.34755. |

3. A crystalline form of 1-((4-(4-Fluoro-2-methyl-1H-indol-5-yloxy)-6-methoxyquino-lin-7-yloxy)methyl)cyclopropanamine according claim 1 exhibiting a XRPD having pattern shown in FIG. 3 comprising 26 characteristic peaks with all intensity % expressed in d values and angles as follows:

| NO. | Angle | d value | Intensity (%) |
|---|---|---|---|
| 1 | 10.892 | 8.11623 | 2.1 |
| 2 | 11.589 | 7.62991 | 6.1 |
| 3 | 12.195 | 7.25174 | 5.9 |
| 4 | 13.344 | 6.62986 | 36.2 |
| 5 | 15.858 | 5.58405 | 31.5 |
| 6 | 16.799 | 5.27326 | 77.9 |
| 7 | 17.640 | 5.02377 | 18.8 |
| 8 | 18.770 | 4.72373 | 11.9 |
| 9 | 19.987 | 4.43884 | 7.2 |
| 10 | 20.650 | 4.29771 | 42.0 |
| 11 | 21.633 | 4.10463 | 15.3 |
| 12 | 23.087 | 3.84934 | 100.0 |
| 13 | 24.356 | 3.65157 | 3.5 |
| 14 | 25.128 | 3.54112 | 14.6 |
| 15 | 25.669 | 3.46768 | 3.8 |
| 16 | 26.607 | 3.34755 | 18.0 |
| 17 | 26.607 | 3.34755 | 3.1 |
| 18 | 29.050 | 3.07132 | 5.7 |
| 19 | 29.797 | 2.99602 | 1.5 |
| 20 | 30.681 | 2.91167 | 4.3 |
| 21 | 31.853 | 2.80718 | 1.2 |
| 22 | 33.524 | 2.67095 | 2.8 |
| 23 | 34.789 | 2.57667 | 2.6 |
| 24 | 35.873 | 2.50131 | 2.2 |
| 25 | 37.391 | 2.40313 | 3.9 |
| 26 | 38.637 | 2.32846 | 1.4. |

4. A pharmaceutical composition that comprises as an active ingredient a compound as defined in claim 1 of the compound and a pharmaceutically acceptable carrier.

5. A method of treating an optometric disease, said method comprising administering a compound as defined in claim 1.

6. A method of treating as claimed in claim 5, wherein an optometric disease is AMD and the combing anti-VEGF antibody is ranibizumab, or the VEGF trap is aflibercep.

7. A method of treating an optometric disease, said method comprising administering a pharmaceutical composition comprising a compound as defined in claim 1 and pharmaceutically acceptable excipients to a subject in need thereof.

8. A method of treating an optometric disease, said method comprising administering a pharmaceutical composition comprising the compound as defined claim 1 with an anti-VEGF antibody or VEGF trap to a subject in need thereof.

9. A process to synthesize 1-((4-(4-Fluoro-2-methyl-1H-indol-5-yloxy)-6-methoxyquino-lin-7-yl-oxy)methyl)cyclopropanamine (AL3818) according to claim 1 where AL3818 can be prepared according to Process A1 when R is H by deprotecting intermediate (Z-1) with HCOONH4 (ammonium formate) and Pd/C in an alcoholic solvent at 25° C.-80° C. for 0.1-4 hours (Z-1) can be prepared by reacting intermediate (X1) with (Y1-1) at the presence of KI or NaI with $K_2CO_3$ in acetone or DMF at a temperature of 60° C.-160° C. for 2-24 hours.

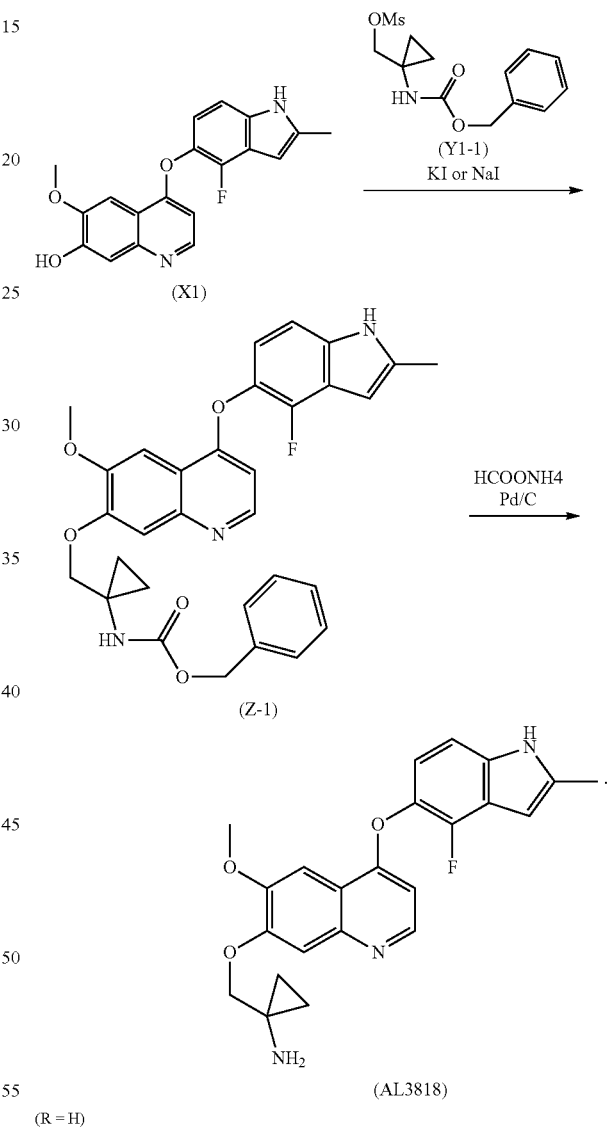

* * * * *

UNITED STATES PATENT AND TRADEMARK OFFICE
CERTIFICATE OF CORRECTION

PATENT NO.      : 9,751,859 B2
APPLICATION NO. : 15/143630
DATED           : September 5, 2017
INVENTOR(S)     : Guoqing Paul Chen et al.

Page 1 of 1

It is certified that error appears in the above-identified patent and that said Letters Patent is hereby corrected as shown below:

In the Specification

In Column 9 at Line 39 (approx.), above "The final" insert --R is selected from H and C1-C6 alkoxy--.

In Column 15 at Line 62, change "-H-" to -- -1H- --.

In Column 16 at Line 58, change "-H-" to -- -1H- --.

In Column 20 at Line 25, change "1 pig" to --1 μg--.

In the Claims

In Column 20 at Line 53 (approx.), in Claim 2, change "-1-methyl-" to -- -2-methyl- --.

In Column 20 at Line 55 (approx.), in Claim 2, change "according claim 1" to --according to claim 1--.

In Column 21 at Line 11 (approx.), in Claim 3, change "according claim 1" to --according to claim 1--.

In Column 21 at Line 47 (approx.), in Claim 5, change "claim 1." to --claim 1 to a subject in need thereof.--.

In Column 21 at Lines 49-50, In Claim 6, change "AMD and the combing anti-VEGF antibody is ranibizumab, or the VEGF trap is aflibercep." to --AMD.--.

Signed and Sealed this
Twentieth Day of February, 2018

Andrei Iancu
*Director of the United States Patent and Trademark Office*